United States Patent
Duffy et al.

(10) Patent No.: US 10,561,497 B2
(45) Date of Patent: Feb. 18, 2020

(54) DELIVERY SYSTEM HAVING A SHORT CAPSULE SEGMENT AND A CINCH MECHANISM AND METHODS OF USE THEREOF

(71) Applicant: Medtronic Vascular, Inc., Santa Rosa, CA (US)

(72) Inventors: Niall Duffy, Galway (IE); Kevin Mauch, Windsor, CA (US)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 288 days.

(21) Appl. No.: 15/452,434

(22) Filed: Mar. 7, 2017

(65) Prior Publication Data

US 2018/0256326 A1    Sep. 13, 2018

(51) Int. Cl.
*A61F 2/24* (2006.01)

(52) U.S. Cl.
CPC .......... *A61F 2/2436* (2013.01); *A61F 2/2409* (2013.01); *A61F 2/2418* (2013.01); *A61F 2/2439* (2013.01); *A61F 2220/0083* (2013.01); *A61F 2250/0069* (2013.01)

(58) Field of Classification Search
CPC .... A61F 2/2409; A61F 2/2418; A61F 2/2436; A61F 2/2439; A61F 2/24; A61F 2/2412; A61F 2/2427; A61F 2/2466; A61F 2220/0083; A61F 2250/0039
See application file for complete search history.

(56) References Cited

U.S. PATENT DOCUMENTS

| | | | |
|---|---|---|---|
| 5,035,706 A | 7/1991 | Giantureo et al. |
| 5,693,084 A | 12/1997 | Chuter |
| 5,776,186 A | 7/1998 | Uflacker |
| 6,280,465 B1 | 8/2001 | Cryer |
| 6,517,550 B1 | 2/2003 | Konya et al. |
| 6,733,521 B2 | 5/2004 | Chobotov et al. |

(Continued)

FOREIGN PATENT DOCUMENTS

WO    2016/122862 A1    8/2016

OTHER PUBLICATIONS

International Search Report and Written Opinion dated May 29, 2018 in corresponding International Patent Application No. PCT/US2018/020913.

*Primary Examiner* — Jocelin C Tanner

(74) *Attorney, Agent, or Firm* — Medler Ferro Woodhouse & Mills PLLC

(57) ABSTRACT

A delivery system including a heart valve prosthesis and a delivery catheter. The delivery catheter includes an outer shaft component, an inner shaft component and a cinch mechanism. The outer shaft component has a capsule segment configured to encircle a first portion of the heart valve prosthesis and to thereby hold the first portion of the heart valve prosthesis in a reduced diameter state for delivery to a treatment site. The cinch mechanism surrounds a second portion of the heart valve prosthesis and is configured to hold the remainder of the heart valve prosthesis in a reduced diameter state for delivery to the treatment site. The capsule segment ends proximal of the cinch mechanism when the delivery catheter is in a delivery configuration. The capsule segment and the cinch mechanism in tandem hold the heart valve prosthesis in the reduced diameter state.

20 Claims, 20 Drawing Sheets

(56) References Cited

U.S. PATENT DOCUMENTS

| | | |
|---|---|---|
| 6,740,111 B1 | 5/2004 | Lauterjung |
| 7,033,390 B2 | 4/2006 | Johnson et al. |
| 7,329,275 B2 | 2/2008 | Yee |
| 7,503,929 B2 | 3/2009 | Johnson et al. |
| 8,403,981 B2 | 3/2013 | Forster et al. |
| 9,034,032 B2 | 5/2015 | McLean et al. |
| 9,034,033 B2 | 5/2015 | McLean et al. |
| 9,039,757 B2 | 5/2015 | McLean et al. |
| 9,125,740 B2 | 9/2015 | Morriss et al. |
| 2005/0119722 A1 | 6/2005 | Styrc et al. |
| 2009/0270974 A1 | 10/2009 | Berez et al. |
| 2010/0249908 A1 | 9/2010 | Chau et al. |
| 2010/0286768 A1* | 11/2010 | Alkhatib ............... A61F 2/2418 623/2.11 |
| 2011/0040366 A1 | 2/2011 | Goetz et al. |
| 2011/0208283 A1* | 8/2011 | Rust ...................... A61F 2/2418 623/1.11 |
| 2012/0277734 A1 | 11/2012 | Goetz et al. |
| 2013/0096664 A1 | 4/2013 | Goetz et al. |
| 2013/0103131 A1 | 4/2013 | Goetz et al. |
| 2013/0231735 A1 | 9/2013 | Deem et al. |
| 2013/0245752 A1 | 9/2013 | Goetz et al. |
| 2013/0325101 A1 | 12/2013 | Goetz et al. |
| 2013/0338755 A1 | 12/2013 | Goetz et al. |
| 2014/0330368 A1 | 11/2014 | Gloss et al. |
| 2015/0112430 A1 | 4/2015 | Creaven et al. |
| 2015/0142100 A1 | 5/2015 | Morriss et al. |
| 2015/0164640 A1 | 6/2015 | McLean et al. |
| 2015/0238315 A1* | 8/2015 | Rabito ................. A61F 2/2436 623/2.11 |
| 2015/0374492 A1 | 12/2015 | Alkhatib |

\* cited by examiner

DELIVERY SYSTEM HAVING A SHORT CAPSULE SEGMENT AND A CINCH MECHANISM AND METHODS OF USE THEREOF

FIELD OF THE INVENTION

The invention relates to valve prostheses and more particularly to delivery systems for a transcatheter heart valve prosthesis.

BACKGROUND OF THE INVENTION

The human heart is a four chambered, muscular organ that provides blood circulation through the body during a cardiac cycle. The four main chambers include the right atrium and right ventricle which supplies the pulmonary circulation, and the left atrium and left ventricle which supplies oxygenated blood received from the lungs to the remaining body. To ensure that blood flows in one direction through the heart, atrioventricular valves (tricuspid and mitral valves) are present between the junctions of the atrium and the ventricles, and semi-lunar valves (pulmonary valve and aortic valve) govern the exits of the ventricles leading to the lungs and the rest of the body. These valves contain leaflets or cusps that open and shut in response to blood pressure changes caused by the contraction and relaxation of the heart chambers. The leaflets move apart from each other to open and allow blood to flow downstream of the valve, and coapt to close and prevent backflow or regurgitation in an upstream manner.

Diseases associated with heart valves, such as those caused by damage or a defect, can include stenosis and valvular insufficiency or regurgitation. For example, valvular stenosis causes the valve to become narrowed and hardened which can prevent blood flow to a downstream heart chamber from occurring at the proper flow rate and may cause the heart to work harder to pump the blood through the diseased valve. Valvular insufficiency or regurgitation occurs when the valve does not close completely, allowing blood to flow backwards, thereby causing the heart to be less efficient. A diseased or damaged valve, which can be congenital, age-related, drug-induced, or in some instances, caused by infection, can result in an enlarged, thickened heart that loses elasticity and efficiency. Some symptoms of heart valve diseases can include weakness, shortness of breath, dizziness, fainting, palpitations, anemia and edema, and blood clots which can increase the likelihood of stroke or pulmonary embolism. Symptoms can often be severe enough to be debilitating and/or life threatening.

Heart valve prostheses have been developed for repair and replacement of diseased and/or damaged heart valves. Such heart valve prostheses can be percutaneously delivered and deployed at the site of the diseased heart valve through catheter-based delivery systems. Such heart valve prostheses can be delivered while in a low-profile or compressed/contracted configuration so that the valve prosthesis can be advanced through the patient's vasculature. Once positioned at the treatment site, the valve prosthesis can be expanded to engage tissue at the diseased heart valve region to, for instance, hold the valve prosthesis in position. While these valve prostheses offer minimally invasive methods for heart valve repair and/or replacement, challenges remain to providing effective, less invasive, smaller crossing profile prosthetic delivery systems, particularly for mitral valve replacement. For example, catheter delivery approaches and techniques for mitral valve replacement may utilized a transseptal approach. However, with the valve prosthesis retained within a capsule of the delivery system, challenges such as capsule travel within the confined space of the left atrium may limit positioning of a heart valve prosthesis in the native mitral valve. Moreover, the capsule adds to the crossing profile of the catheter. Catheter crossing profile, especially for inter-atrial septum puncture, limit both the feasibility of heart valve prosthetic delivery as well as the size of the heart valve prosthesis.

Embodiments hereof are directed to a delivery catheter for heart valve replacement that addresses some of the challenges described above.

BRIEF SUMMARY OF THE INVENTION

Embodiments hereof relate to a delivery catheter for delivering a heart valve prosthesis. The delivery catheter includes a capsule segment configured to encircle a first portion of the heart valve prosthesis and to thereby hold the first portion of the heart valve prosthesis in a reduced diameter state for delivery to a treatment site, and a cinch mechanism surrounding a second portion of the heart valve prosthesis and configured to hold the remainder of the heart valve prosthesis in a reduced diameter state for delivery to the treatment site. The capsule segment and the cinch mechanism are disposed longitudinally adjacent to each other and do not overlap when the delivery catheter is in a delivery configuration.

Embodiments hereof also relate to a delivery catheter for a heart valve prosthesis that includes a first tubular shaft with a capsule segment, a second tubular shaft having a proximal segment positioned within the first tubular shaft and a distal segment disposed distal of the capsule segment of the first tubular shaft, and a cinch mechanism disposed about the distal segment of the second tubular shaft. The capsule segment and the cinch mechanism are configured in tandem to hold a heart valve prosthesis in a reduced diameter state.

Embodiments hereof also relate to a method of deploying a heart valve prosthesis includes loading a heart valve prosthesis onto a delivery catheter. The delivery catheter includes a capsule segment and a cinch mechanism that are configured in tandem to hold the heart valve prosthesis in a reduced diameter state. The capsule segment and the cinch mechanism are disposed longitudinally adjacent to each other and do not overlap when the delivery catheter is in a delivery configuration. The delivery catheter is positioned with the heart valve prosthesis in the reduced diameter state at a native heart valve. The capsule segment is longitudinally repositioned to permit a first portion of the heart valve prosthesis to return to an expanded state. The cinch mechanism is released to permit a second portion of the heart valve prosthesis to return to an expanded state.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, wherein like reference numbers indicate identical or functionally similar elements. Unless otherwise indicated, the terms "distal" and "proximal" are used in the following description with respect to a position or direction relative to the treating clinician. "Distal" and "distally" are positions distant from or in a direction away from the clinician, and "proximal" and "proximally" are positions near or in a direction toward the clinician. In addition, the term "self-expanding" is used in the following description and is intended to convey that the structures are shaped or formed from a material that can be provided with a mechanical memory to return the structure from a compressed or constricted delivery configuration/state to an expanded deployed configuration/state. Non-exhaustive exemplary self-expanding materials include stainless steel, a pseudo-elastic metal such as a nickel titanium alloy or nitinol, various polymers, or a so-called super alloy, which may have a base metal of nickel, cobalt, chromium, or other metal. Mechanical memory may be imparted to a wire or scaffold structure by thermal treatment to achieve a spring temper in stainless steel, for example, or to set a shape memory in a susceptible metal alloy, such as nitinol. Various polymers that can be made to have shape memory characteristics may also be suitable for use in embodiments hereof to include polymers such as polynorborene, trans-polyisoprene, styrene-butadiene, and polyurethane. As well poly L-D lactic copolymer, oligo caprylactone copolymer and polycyclooctene can be used separately or in conjunction with other shape memory polymers.

The following detailed description is merely exemplary in nature and is not intended to limit the invention or the application and uses of the invention. Although the description of embodiments hereof is in the context of delivery systems for delivering a valve prosthesis within a native mitral valve, the delivery systems described herein can also be used in other valves of the body, such as for delivering a valve prosthesis within a native tricuspid valve, a native aortic valve, or for delivering a valve prosthesis within a failed previously-implanted prosthesis. Furthermore, there is no intention to be bound by any expressed or implied theory presented in the preceding technical field, background, brief summary or the following detailed description.

Figure 1:
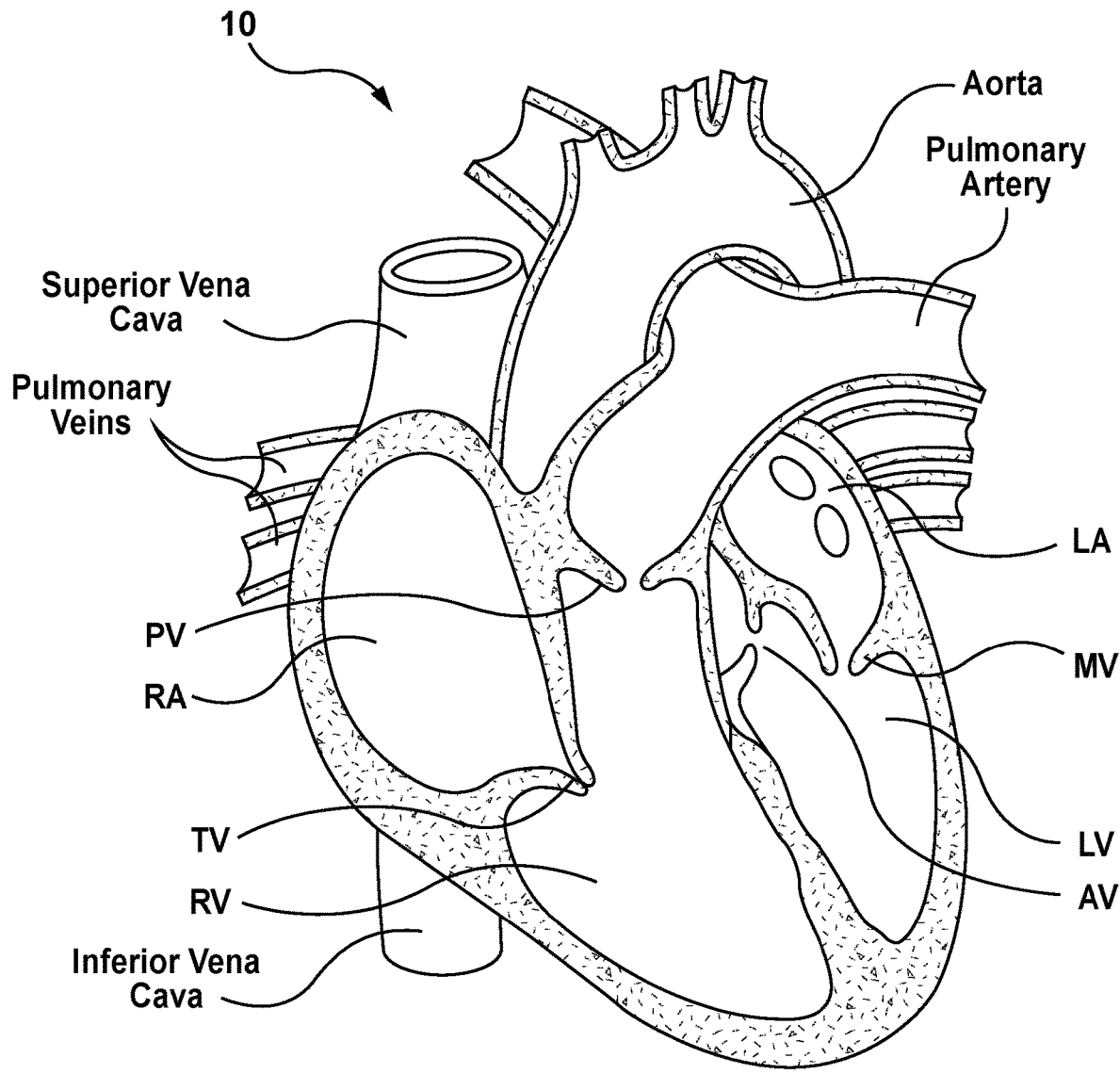
FIG. 1 is a schematic sectional illustration of a mammalian heart having native valve structures.
Figure 2B:
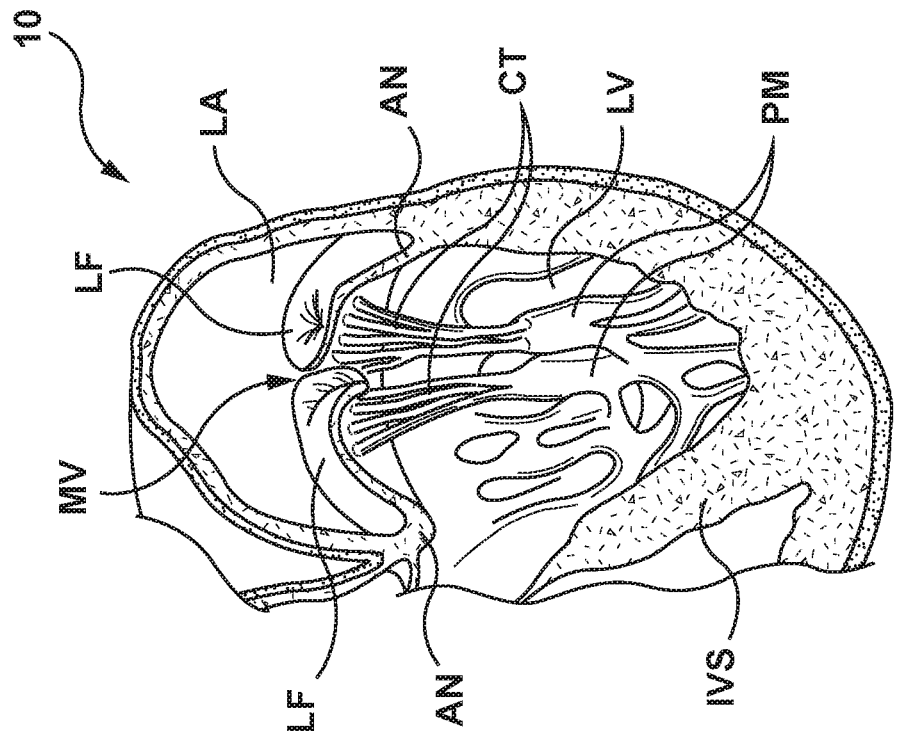
FIG. 2B is a schematic sectional illustration of the left ventricle of a heart having a prolapsed mitral valve in which the leaflets do not sufficiently co-apt and which is suitable for replacement with a valve prosthesis via a delivery system in accordance with embodiments hereof.
Figure 2A:
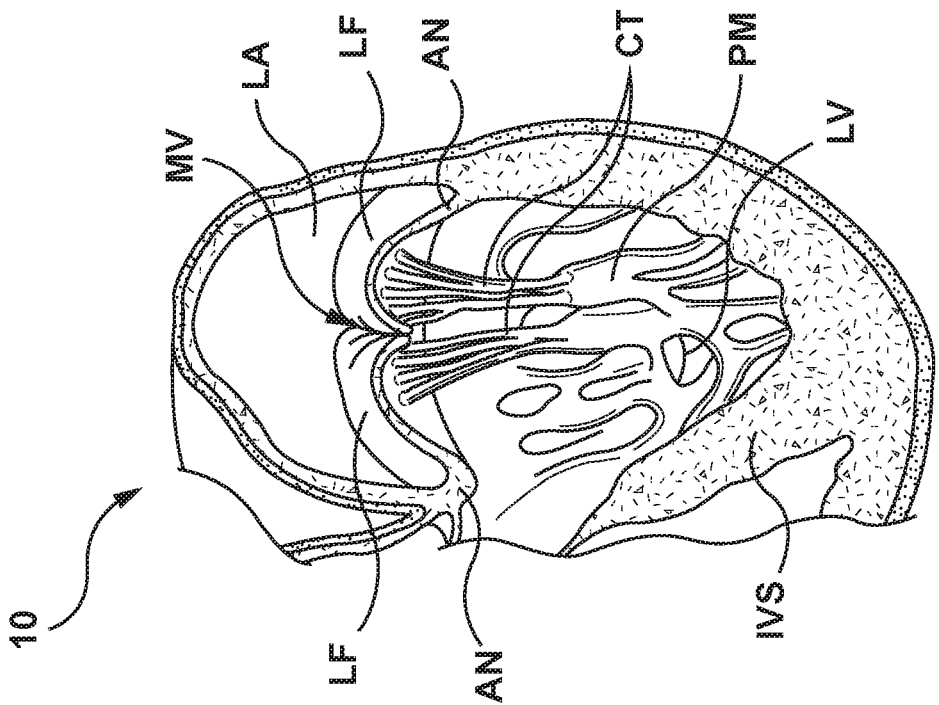
FIG. 2A is a schematic sectional illustration of a left ventricle of a mammalian heart showing anatomical structures and a native mitral valve.

FIG. 1 is a schematic sectional illustration of a mammalian heart 10 that depicts the four heart chambers (right atrium RA, right ventricle RV, left atrium LA, left ventricle LV) and native valve structures (tricuspid valve TV, mitral valve MV, pulmonary valve PV, aortic valve AV). FIG. 2A is a schematic sectional illustration of a left ventricle LV of a mammalian heart 10 showing anatomical structures and a native mitral valve MV. Referring to FIGS. 1 and 2A together, the heart 10 comprises the left atrium LA that receives oxygenated blood from the lungs via the pulmonary veins. The left atrium LA pumps the oxygenated blood through the mitral valve MV and into the left ventricle LV during ventricular diastole. The left ventricle LV contracts during systole and blood flows outwardly through the aortic valve AV, into the aorta and to the remainder of the body.

In a healthy heart, as shown in FIG. 2A, the leaflets LF of the native mitral valve MV meet evenly at the free edges or "coapt" to close and prevent back flow of blood into the left atrium LA during contraction of the left ventricle LV. The tissue of the leaflets LF attach the surrounding heart structure via a dense fibrous ring of connective tissue called an annulus AN which is distinct from both the tissue of the leaflets LF as well as the adjoining muscular tissue of the heart wall. In general, the connective tissue at the annulus AN is more fibrous, tougher and stronger than leaflet tissue. The flexible tissue of the leaflets LF of the native mitral valve MV are connected to papillary muscles PM, which extend upwardly from the lower wall of the left ventricle LV and the interventricular septum IVS, via branching tendons called chordae tendinae CT. In a heart 10 having a prolapsed mitral valve MV in which the leaflets LF do not sufficiently coapt or meet, as shown in FIG. 2B, leakage from the left ventricle LV into the left atrium LA will occur. Several structural defects can cause the mitral leaflets LF to prolapse, and subsequent regurgitation to occur, including ruptured chordae tendinae CT, impairment of papillary muscles PM (e.g., due to ischemic heart disease), and enlargement of the heart and/or mitral valve annulus AN (e.g., cardiomyopathy).

Embodiments hereof are related to a delivery system suitable for intravascular delivery of a heart valve prosthesis to a native valve in a heart of a patient. In some embodiments, delivery catheters and methods are presented for the treatment of valve disease as part of procedure steps for minimally invasive implantation of an artificial or prosthetic heart valve, such as a mitral valve. For example, a heart delivery system, in accordance with embodiments described herein, can be used to percutaneously direct and deliver a mitral valve prosthesis via an intravascular retrograde approach across an aortic valve, into a left ventricle and across a diseased or damaged mitral valve in a patient, such as in a patient suffering from mitral valve prolapse illustrated in FIG. 2B. In another embodiment, a heart delivery system, in accordance with embodiments described herein, can be used to direct and deliver an aortic valve prosthesis via an aortic approach across an aortic arch, into an aortic sinus and across a diseased or damaged aortic valve in a patient. In further embodiments, the delivery systems and delivery catheters disclosed herein are suitable for prosthetic heart valve delivery across other diseased or damaged natural heart valves or prior implanted prosthetic heart valves, such as tricuspid, and pulmonary heart valves.

Figure 3A:
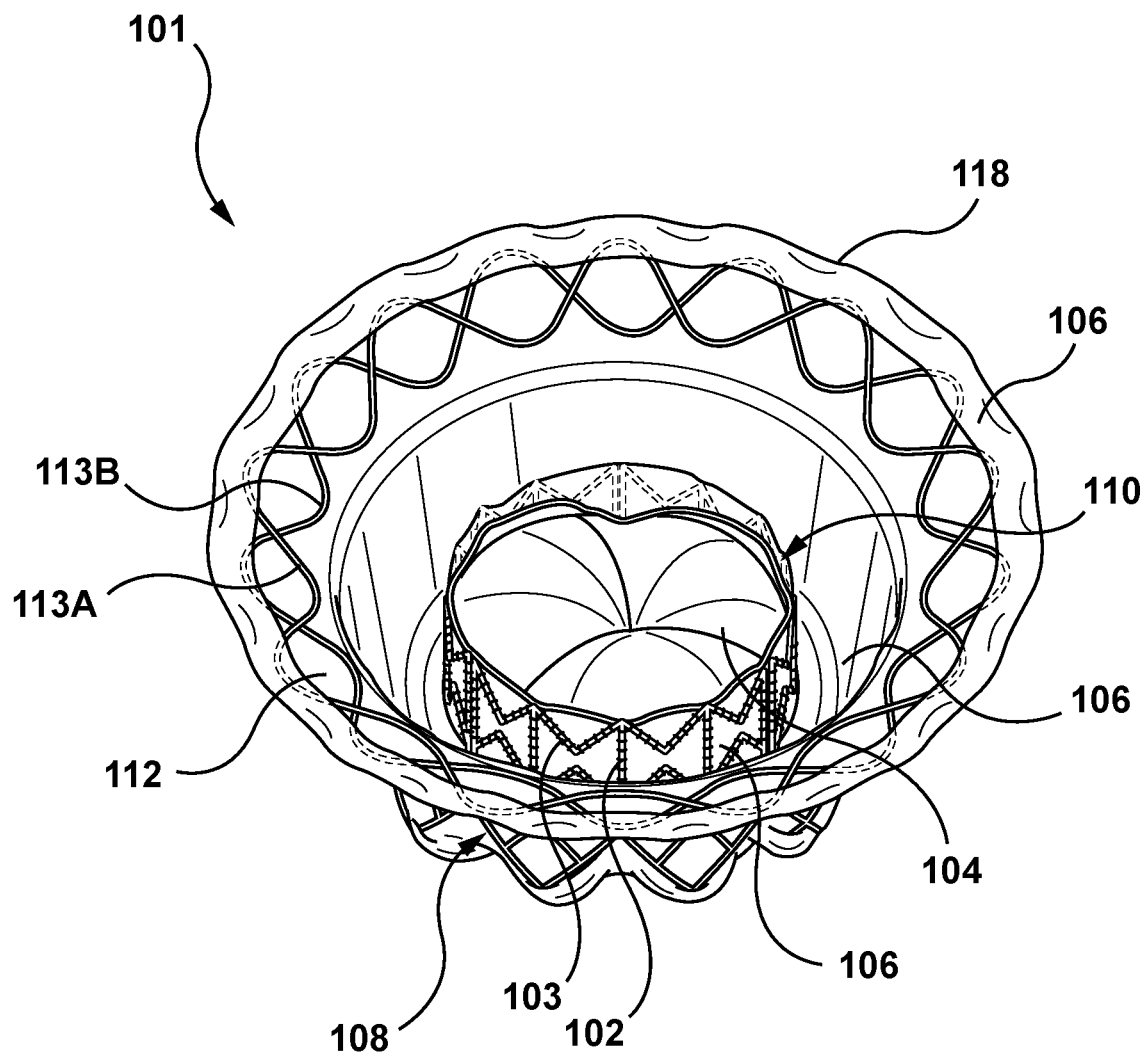
FIG. 3A is a perspective view of an exemplary heart valve prosthesis for use in embodiments hereof, the heart valve prosthesis in its expanded or deployed configuration.
Figure 3C:
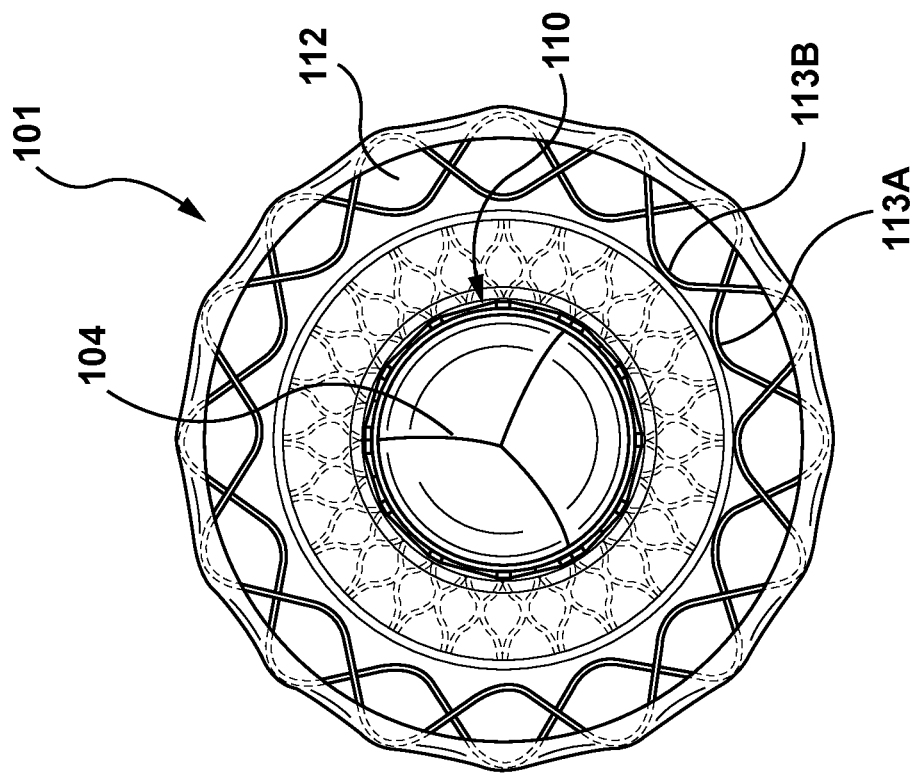
FIG. 3C is a top view of the heart valve prosthesis of FIG. 3A, the heart valve prosthesis in its expanded or deployed configuration.
Figure 3B:
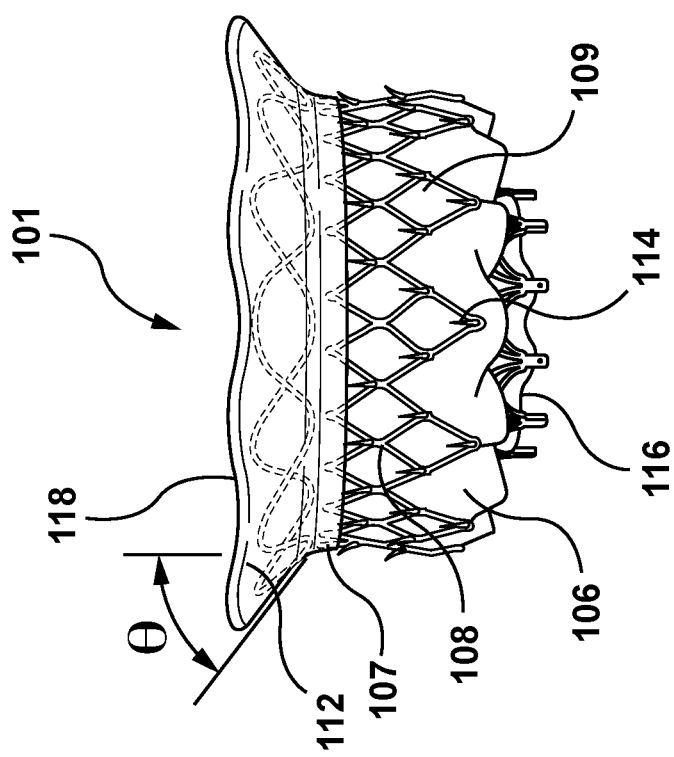
FIG. 3B is a side view of the heart valve prosthesis of FIG. 3A, the heart valve prosthesis in its expanded or deployed configuration.

FIGS. 3A, 3B, 3C are perspective, side, and top views, respectively, of an exemplary heart valve prosthesis 101 for use in embodiments hereof, wherein the valve prosthesis is in an expanded or deployed configuration in accordance with an embodiment hereof. Heart valve prosthesis 101 is illustrated herein in order to facilitate description of delivery catheters and systems to be utilized in conjunction therewith according to embodiments hereof. It is understood that any number of alternate heart valve prostheses can be used with the methods and devices described herein. Heart valve prosthesis 101 is merely exemplary and is similar to heart valve prostheses described in more detail in U.S. Pat. No. 9,034,032 to McLean et al., which is herein incorporated by reference in its entirety. Other non-limiting examples of transcatheter valve prostheses useful with systems and methods of the present disclosure are described in U.S. Patent Application Publication Nos. 2012/0101572 to Kovalsky et al., 2012/0035722 to Tuval U.S. Pat. Appl. Pub. No. 2006/0265056 to Nguyen et al., U.S. Pat. Appl. Pub. No. 2007/05409266 to Birdsall, U.S. Pat. Appl. Pub. No. 2007/05409269 to Dolan et al., and U.S. Pat. Appl. Pub. No. 2008/00713548 to Tuval, each of which is incorporated by reference herein in its entirety and illustrate heart valve prostheses configured for placement in a mitral valve.

As shown in FIGS. 3A-3C, heart valve prosthesis 101 includes a flexible anchoring member 108 at least partially surrounding and coupled to an inner valve support 110. Heart valve prosthesis 101 further includes a prosthetic valve component 104 coupled to, mounted within, or otherwise carried by valve support 110. Heart valve prosthesis 101 is configured for placement within a native mitral valve and includes a downstream end or outflow portion 116 and an upstream end or inflow portion 118. Heart valve prosthesis 101 also includes one or more sealing members 106 and tissue engaging elements 114. For example, tissue engaging elements 114 may be spikes or barbs disposed on an outer wall or surface of anchoring member 108 and extend in an upward and/or radially outward direction to engage, and in some embodiments, penetrate the native tissue to facilitate retention or maintain position of the device in a desired implanted location. In another specific embodiment, sealing members 106 may extend around an inner wall or surface of anchoring member 108 and/or around an inner wall or surface of valve support 110 to prevent paravalvular leaks between heart valve prosthesis 101 and the native tissue and/or between anchoring member 108 and valve support 110. Additionally, valve support 110 may have a plurality of coupling features (not shown), such as eyelets, around an upstream end to facilitate loading, retention and deployment of heart valve prosthesis 101 within and from a delivery catheter (not shown), as further described herein.

Anchoring member 108 is a generally tubular stent or scaffold. In an embodiment hereof as shown in FIGS. 3A-3C, anchoring member 108 has a funnel-like or hyperboloid shape or profile. Further, in an embodiment hereof as shown in FIGS. 3A-3C, anchoring member 108 is a generally tubular stent or scaffold with diamond-shaped openings 109 that may be formed by a laser-cut manufacturing method and/or another conventional stent/scaffold forming method as would be understood by one of ordinary skill in the art. For example, anchoring member 108 may be laser cut from a single metal tube into the desired geometry, creating a tubular scaffold of interconnected struts that form diamond-shaped openings 109. Anchoring member 108 may then be shaped into a desired configuration, e.g. funnel-like or hyperboloid shape, using known shape-setting techniques for such materials. As will be understood by one of ordinary skill in the art, the stent or scaffold of a valve prosthesis may have other configurations such as a metallic, polymeric, or fabric mesh or a woven construction. In another embodiment hereof, anchoring member 108 may include a plurality of posts connected circumferentially by a plurality of struts as described herein with respect to valve support 110.

Heart valve prosthesis 101 further includes a brim 112. Brim 112 is disposed at inflow portion 118 of heart valve prosthesis 101 and is attached to and extends from an inflow end 107 of anchoring member 108. Brim 112 is a flared lip or ridge of anchoring member 108 that extends at least partially radially outward relative to anchoring member 108. As formed and as best shown in the side view of FIG. 3B, brim 112 may be disposed at an angle θ relative to the outer wall or surface of anchoring member 108, with angle θ ranging between 30 degrees and 90 degrees. In an embodiment hereof, angle θ is approximately 45 degrees, wherein approximately as used herein includes a tolerance of 5 degrees. In an embodiment hereof as shown in FIGS. 3A-3C, brim 112 includes two sinusoidal rings 113A, 113B and sealing member 106 disposed over or covering at least on a downstream surface of sinusoidal rings 113A, 113B. Sinusoidal rings 113A, 113B are disposed out of phase relative to each other, and may be woven together or may be disposed in an overlapping manner and coupled together.

Valve support 110 is also a generally cylindrical stent or scaffold that supports prosthetic valve component 104 within the interior thereof. In some embodiments, valve support 110 includes a plurality of posts 102 connected circumferentially by a plurality of struts 103. Posts 102 and struts 103 may be arranged in a variety of geometrical patterns that may expand and provide sufficient resilience and column strength for maintaining the integrity of prosthetic valve component 104. For example, posts 102 may extend longitudinally across multiple rows of struts 103 to provide column strength to the valve support 110. Generally, the plurality of posts 102 may extend along an axial direction generally parallel to the longitudinal axis and the struts 103 may extend circumferentially around and transverse to the longitudinal axis. As will be understood by one of ordinary skill in the art, the stent or scaffold of a valve prosthesis may have other configurations such as a metallic, polymeric, or fabric mesh or a woven construction. In another embodiment hereof, valve support 110 may be laser cut from a single metal tube into the desired geometry, creating a tubular scaffold of interconnected struts.

In embodiments hereof, both anchoring member 108 and valve support 110 are self-expanding to return to an expanded deployed state from a compressed or constricted delivery state and may be made from stainless steel, a pseudo-elastic metal such as a nickel titanium alloy or Nitinol, or a so-called super alloy, which may have a base metal of nickel, cobalt, chromium, or other metal. "Self-expanding" as used herein means that a structure/component has a mechanical memory to return to the expanded or deployed configuration as described herein. Alternatively, heart valve prosthesis 101 may be balloon-expandable as would be understood by one of ordinary skill in the art. Whether valve support 110 is self-expanding or balloon-expandable, heart valve prosthesis 101 has a reduced diameter state for delivery within a delivery system and a radially expanded configuration for deployment within an annulus of the native valve site.

As previously mentioned, heart valve prosthesis 101 includes prosthetic valve component 104 within the interior of valve support 110. In an embodiment hereof, prosthetic valve component 104 is positioned adjacent to the inflow end of valve support 110. Prosthetic valve component 104 is configured as a one-way valve to allow blood flow in one direction and thereby regulate blood flow therethrough. Prosthetic valve component 104 is capable of blocking flow in one direction to regulate flow therethrough via valve leaflets that may form a bicuspid or tricuspid replacement valve. More particularly, if heart valve prosthesis 101 is configured for placement within a native valve having two leaflets such as the mitral valve, prosthetic valve component 104 includes two valve leaflets to form a bicuspid replacement valve that closes with pressure on the outflow and opens with pressure on the inflow. In other embodiments in accordance herewith, the prosthetic valve component may be a tricuspid replacement valve or may be a single leaflet replacement valve. The valve leaflets are sutured or otherwise securely and sealingly attached to an inner circumference of valve support 110 and/or sealing members 106 which encloses or lines valve support 110 as would be known to one of ordinary skill in the art of prosthetic tissue valve construction.

The valve leaflets may be made of pericardial material; however, the leaflets may instead be made of another material. Natural tissue for heart valve prosthesis leaflets for use in prosthetic valve component 104 may be obtained from, for example, heart valves, aortic roots, aortic walls, aortic leaflets, pericardial tissue, such as pericardial patches, bypass grafts, blood vessels, intestinal submucosal tissue, umbilical tissue and the like from humans or animals, such as tissue from bovine, equine or porcine origins. Synthetic materials suitable for use as heart valve prosthesis leaflets in embodiments hereof include DACRON® polyester commercially available from Invista North America S.A.R.L. of Wilmington, Del., polyurethane, Gore-Tex or other cloth materials, nylon blends, polymeric materials, and vacuum deposition nitinol fabricated materials. One polymeric material from which the replacement valve leaflets may be made is an ultra-high molecular weight polyethylene material commercially available under the trade designation DYNEEMA from Royal DSM of the Netherlands. With certain prosthetic leaflet materials, it may be desirable to coat one or both sides of the replacement valve leaflet with a material that will prevent or minimize overgrowth. It is further desirable that the prosthetic leaflet material is durable and not subject to stretching, deforming, or fatigue.

Sealing members 106 are formed from a suitable graft material such as a natural or biological material such as pericardium or another membranous tissue such as intestinal submucosa. Alternatively, sealing members 106 may be a low-porosity woven fabric, such as polyester, Dacron fabric, or PTFE, which creates a one-way fluid passage when attached to the stent. In one embodiment, sealing members 106 may be a knit or woven polyester, such as a polyester or PTFE knit, which can be utilized when it is desired to provide a medium for tissue ingrowth and the ability for the fabric to stretch to conform to a curved surface. Polyester velour fabrics may alternatively be used, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example.

Figure 4:
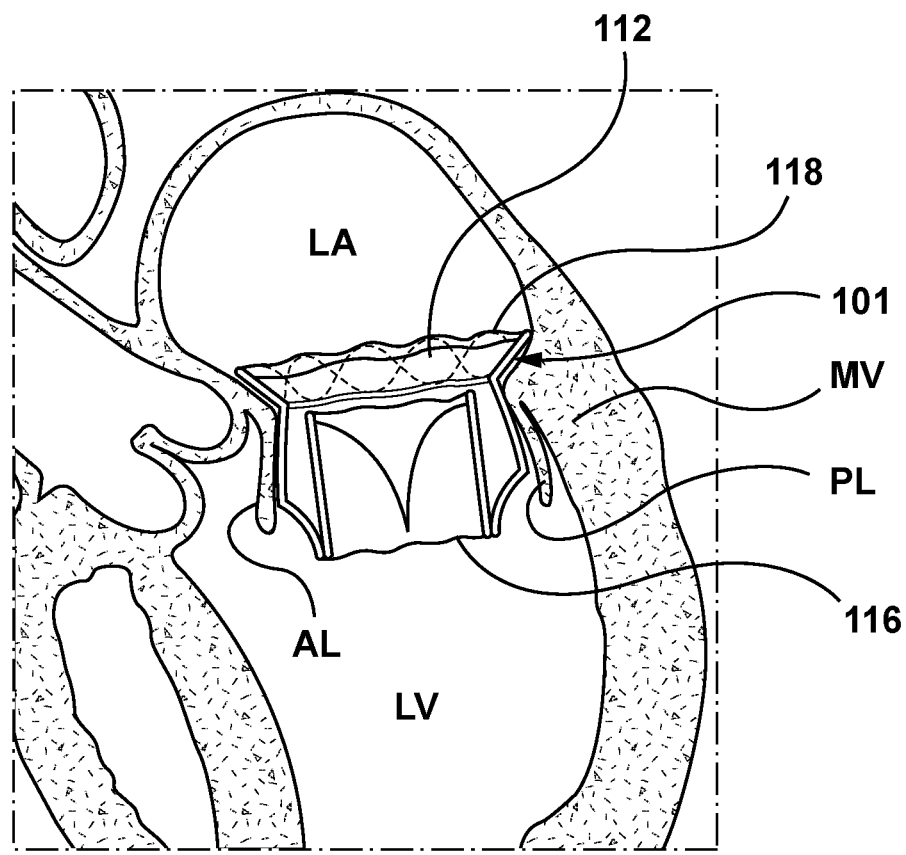
FIG. 4 is a sectional view illustration of the heart valve prosthesis of FIG. 3A implanted within an annulus of a native mitral valve.

FIG. 4 is an illustration of heart valve prosthesis 101 implanted within a native mitral heart valve, which is shown in section. Heart valve prosthesis 101 is shown deployed within a native mitral valve, with downstream end or outflow portion 116 thereof extending into the left ventricle and upstream end or inflow portion 118 including at least brim 112 thereof extending into the left atrium. When heart valve prosthesis 101 is deployed within the valve annulus of a native heart valve, valve support 110 and anchoring member 108 expands within native valve leaflets, posterior leaflet PL and anterior leaflet AL, of the patient's defective valve, retaining the native valve leaflets in a permanently open state.

Figure 5:
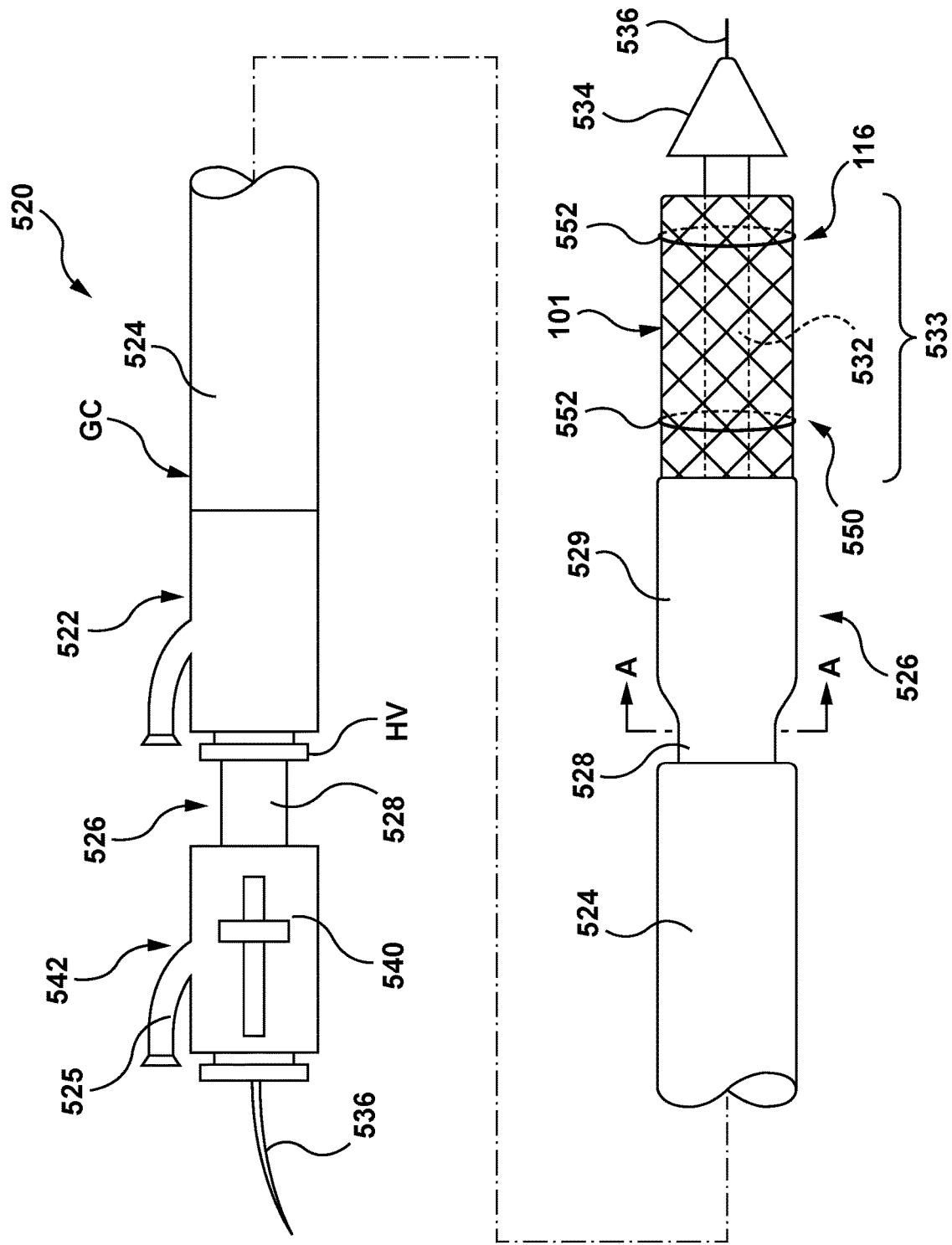
FIG. 5 is a side view illustration of a delivery system configured to deliver the heart valve prosthesis of FIG. 3A according to embodiments hereof, wherein the delivery system includes a capsule segment and a cinch mechanism that are configured in tandem to hold the heart valve prosthesis in a reduced diameter state and the heart valve prosthesis is shown in its reduced diameter state for delivery thereof.
Figure 5A:
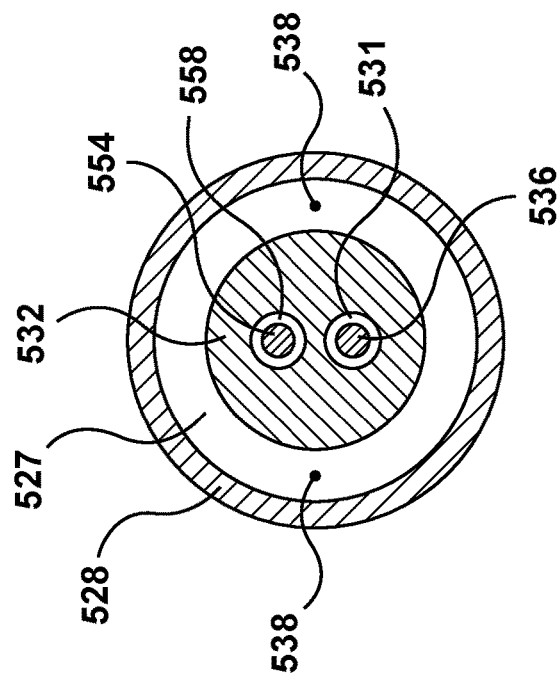
FIG. 5A is a cross-sectional view taken along line A-A of FIG. 5.

FIG. 5 is a side view illustration of a delivery system 520 according to an embodiment hereof which may be used to deliver and deploy heart valve prosthesis 101 disclosed herein to the heart of a patient. FIG. 5A is a cross-sectional view taken along line A-A of FIG. 5. As will be described in more detail herein, delivery system 520 includes a capsule segment 529 and a cinch mechanism 550 that are configured in tandem to hold heart valve prosthesis 101 in a reduced diameter state. Capsule segment 520 is relatively short and is configured to hold only inflow portion 118 of heart valve prosthesis 101 in a reduced diameter state for delivery and distal thereto the remainder of heart valve prosthesis 101 is held in a reduced diameter state by cinch mechanism 550. Capsules of longer lengths are relatively rigid and cannot bend the requisite angle during transseptal delivery within the left atrium, and also are too long to be fully retracted within the left atrium during deployment. As will be described in more detail herein with respect to FIG. 8, the relatively short length of capsule segment 529 permits bending of the distal portion of delivery system 520 during delivery, for example during transeptal delivery thereof within the left atrium, and also eases space constraints during retraction thereof during deployment, for example during retraction within the left atrium.

More particularly, with reference to FIG. 5, delivery system 520 includes a guiding catheter GC and a delivery catheter 526. Guiding catheter GC has a handle 522 coupled to a delivery shaft 524, which in one embodiment is 34 F or less, and in another embodiment, 28 F or less in diameter. Guiding catheter GC may be steerable or preshaped in a configuration suitable for the particular approach to the target valve. Delivery catheter 526 is placed through a hemostasis valve HV on a proximal end of guiding catheter GC.

Delivery catheter 526 is depicted in a delivery configuration in FIG. 5 with heart valve prosthesis 101 loaded within capsule segment 529 of the delivery system. As best shown in FIG. 5A, delivery catheter 526 includes a first tubular shaft or outer shaft component 528 defining a lumen 527 therethrough and a second tubular shaft or inner shaft component 532 defining a first lumen 531 and a second lumen 558 therethrough. Inner shaft component 532 is concentrically slidably disposed within lumen 527 of outer shaft component 528. A nosecone or distal tip component 534 is attached to a distal end of inner shaft component 532. First lumen 531 of inner shaft component 532 may be sized to slidingly receive a guidewire 536 such that delivery catheter 526 may be tracked over the guidewire during delivery of heart valve prosthesis 101. Stated another way, a guidewire lumen of delivery catheter 526 is defined by inner shaft component 532 and distal tip component 534. Second lumen 558 is sized to slidingly receive a release pin 554 which will be described in more detail herein with respect to FIG. 6.

Outer shaft component 528 includes capsule segment 529 which forms a distalmost portion or segment thereof. An elongated proximal portion or segment of inner shaft component 532 is disposed or positioned within outer shaft component 528 and a distal portion or segment 533 of inner shaft component 532 extends distally of capsule segment 529 of outer shaft component 528. Capsule segment 529 functions to protect, secure, and compressively retain a first portion of heart valve prosthesis 101 for delivery. More particularly, capsule segment 529 is configured to encircle a first portion of heart valve prosthesis 101 and to thereby hold or compressively retain the first portion of heart valve prosthesis 101 in a reduced diameter state for delivery to a treatment site. In an embodiment hereof, the first portion is inflow portion 118 of heart valve prosthesis 101 (shown on FIGS. 3 and 4) and includes brim 112 of heart valve prosthesis 101. Outer shaft component 528 is proximally retractable relative to inner shaft component 532 to release and deploy brim 112 of heart valve prosthesis 101 from capsule segment 529. More particularly, in order to be proximally retractable, outer shaft component 528 is coupled to a retraction mechanism 540 on a handle 542 of delivery catheter 526. Various retraction mechanisms 540 may be used, such as an axially-slidable lever, a rotatable rack and pinion gear, or other known mechanisms.

Capsule segment 529 is described herein as an integral or continuous distalmost portion or segment of outer shaft component 528. However, in another embodiment hereof (not shown), capsule segment 529 is formed as a separate component from outer shaft component 528 as described in U.S. Patent Publication No. 2011/0245917 to Savage et al., U.S. Patent Publication No. 2011/0251675 to Dwork, U.S. Patent Publication No. 2011/0251681 to Shipley et al., U.S. Patent Publication No. 2011/0251682 to Murray, III et al., and/or U.S. Patent Publication No. 2011/0264202 to Murray, III et al., each of which is herein incorporated by reference in its entirety.

A second portion of heart valve prosthesis 101 is disposed along distal segment 533 of inner shaft component 532. In an embodiment hereof, the second portion includes outflow portion 116 of heart valve prosthesis 101 (shown on FIGS. 3 and 4) and includes anchoring member 108 and valve support 110 of heart valve prosthesis 101. Cinch mechanism 550 surrounds or encircles the second portion of heart valve prosthesis 101 and is configured to hold the remainder of the heart valve prosthesis (i.e., the remaining length of heart valve prosthesis 101 distal to capsule segment 529) in a reduced diameter state for delivery to the treatment site. Due to cinch mechanism 550, delivery catheter 526 beneficially does not include or require a long retractable capsule for compressing the second or outflow portion 116 of heart valve prosthesis 101, and therefore may be more efficiently utilized within the confines of native anatomy having small or restricted space such as but not limited to the left atrium. Thus, capsule segment 529 compressively holds or retains the first or inflow portion 118 of heart valve prosthesis 101 in a reduced diameter state for delivery, while cinch mechanism 550 compressive holds or retains the second or outflow portion 116 of heart valve prosthesis 101 in a reduced diameter state for delivery. Stated another way, capsule segment 529 and cinch mechanism 550 are configured in tandem to hold heart valve prosthesis 101 in a reduced diameter state. Capsule segment 529 and cinch mechanism 550 are disposed longitudinally adjacent to each other and do not overlap when delivery catheter 526 is in a delivery configuration. As used in this embodiment, "do not overlap" means that capsule segment 529 does not cover the second or outflow portion 116 of heart valve prosthesis 101 when delivery catheter 526 is in a delivery configuration and cinch mechanism 550 does not hold or retain the first or inflow portion 118 of heart valve prosthesis 101 in a reduced diameter state for delivery when delivery catheter 526 is in a delivery configuration. Capsule segment 529 is of a relatively short length, covering only the first or inflow portion 118 of heart valve prosthesis 101 which includes brim 112, and does not cover the second or outflow portion 116 of heart valve prosthesis 101 which includes anchoring member 108 and valve support 110 when the delivery catheter is in a delivery configuration. In an embodiment hereof, capsule segment 529 may range between 30 mm to 40 mm in length. Capsule segment 529 ends proximal of cinch mechanism 550 when delivery catheter 526 is in a delivery configuration. Delivery catheter 526 permits a two-stage deployment of heart valve prosthesis 101 because capsule segment 529 is proximally retractable relative to inner shaft component 532 to permit the first or inflow portion 118 of heart valve prosthesis 101 to return to an expanded or deployed state and cinch mechanism 550 is releasable to permit the second or outflow portion 116 of heart valve prosthesis to return to an expanded or deployed state as will be described in more detail herein with respect to FIGS. 8-11.

Figure 6:
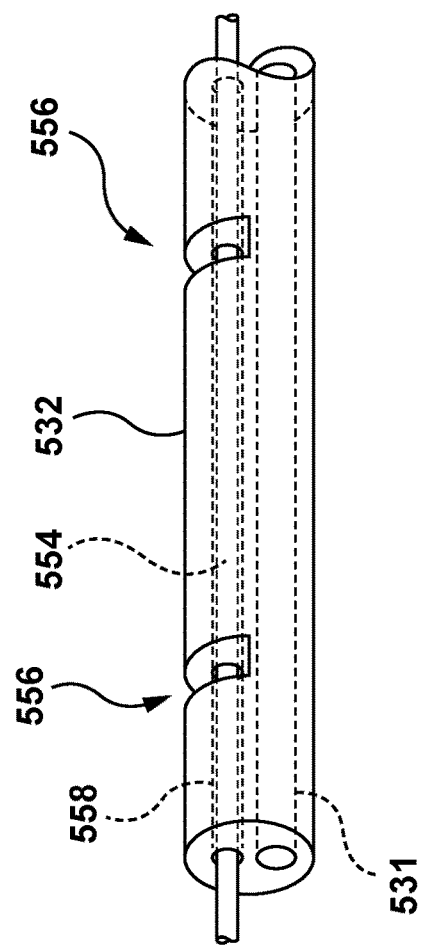
FIG. 6 is a perspective view of a portion of an inner shaft component of the delivery system of FIG. 5, wherein the inner shaft component is removed from the delivery system for purposes of illustration only.

Cinching mechanism 550 will now be described in more detail with additional reference to FIG. 6, which is a perspective view of a portion of inner shaft component 532 removed from the delivery system for purposes of illustration only. Cinch mechanism 550 includes release pin 554 and one or more suture(s) or cord(s) 552 coupled thereto. Suture(s) 552 extend to a proximal end of delivery catheter 526 and are releasable to permit the second or outflow portion 116 of heart valve prosthesis 101 to return to an expanded or deployed state. More particularly, suture(s) 552 are disposed about the second or outflow portion 116 of heart valve prosthesis 101 such that pulling suture(s) 552 controls constriction/compression of the second or outflow portion 116 of heart valve prosthesis 101 and releasing/removing suture(s) 552 controls expansion/deployment of the second or outflow portion 116 of heart valve prosthesis 101. In an embodiment, cinch mechanism 550 includes two suture(s) 552, as shown in FIG. 5, or a single suture 552 may be utilized that forms two loops. Each suture 552 encircles or extends circumferentially around an outer surface of the second or outflow portion 116 of heart valve prosthesis 101, such that suture(s) 552 constrain the second or outflow portion 116 of heart valve prosthesis 101 in the reduced diameter state, releasably coupling the second or outflow portion 116 of heart valve prosthesis 101 to inner shaft component 532. Each suture 552 further extends through a respective notch 556 (see FIG. 6) and couples with release pin 554 disposed within second lumen 558 of inner shaft 532. Release pin 554 is operably coupled to handle 542 at a proximal end (not shown) and is slidable or translatable relative to inner shaft 532. Cinch mechanism 550 is configured such that remote actuation of release pin 554 (e.g., via an actuator such as a knob, pin, or lever carried by handle 542) with the second or outflow portion 116 of heart valve prosthesis 101 in the reduced diameter state controllably releases suture(s) 552 such that the second or outflow portion 116 of heart valve prosthesis 101 radially expands to the expanded configuration. In an embodiment, suture(s) 552 may be formed from a monofilament or plastic suture material, such as polypropylene. Further details and examples of suitable cinch mechanism assemblies for retaining self-expanding valve prostheses are described in U.S. Patent Publication No. 2014/0330368 to Gloss, which is incorporated herein by reference in its entirety. In another embodiment hereof (not shown), suture(s) 552 may be securable about and releasable from the second or outflow portion 116 of heart valve prosthesis 101 by one of a slip knot mechanism or other slow release mechanism.

Figure 7:
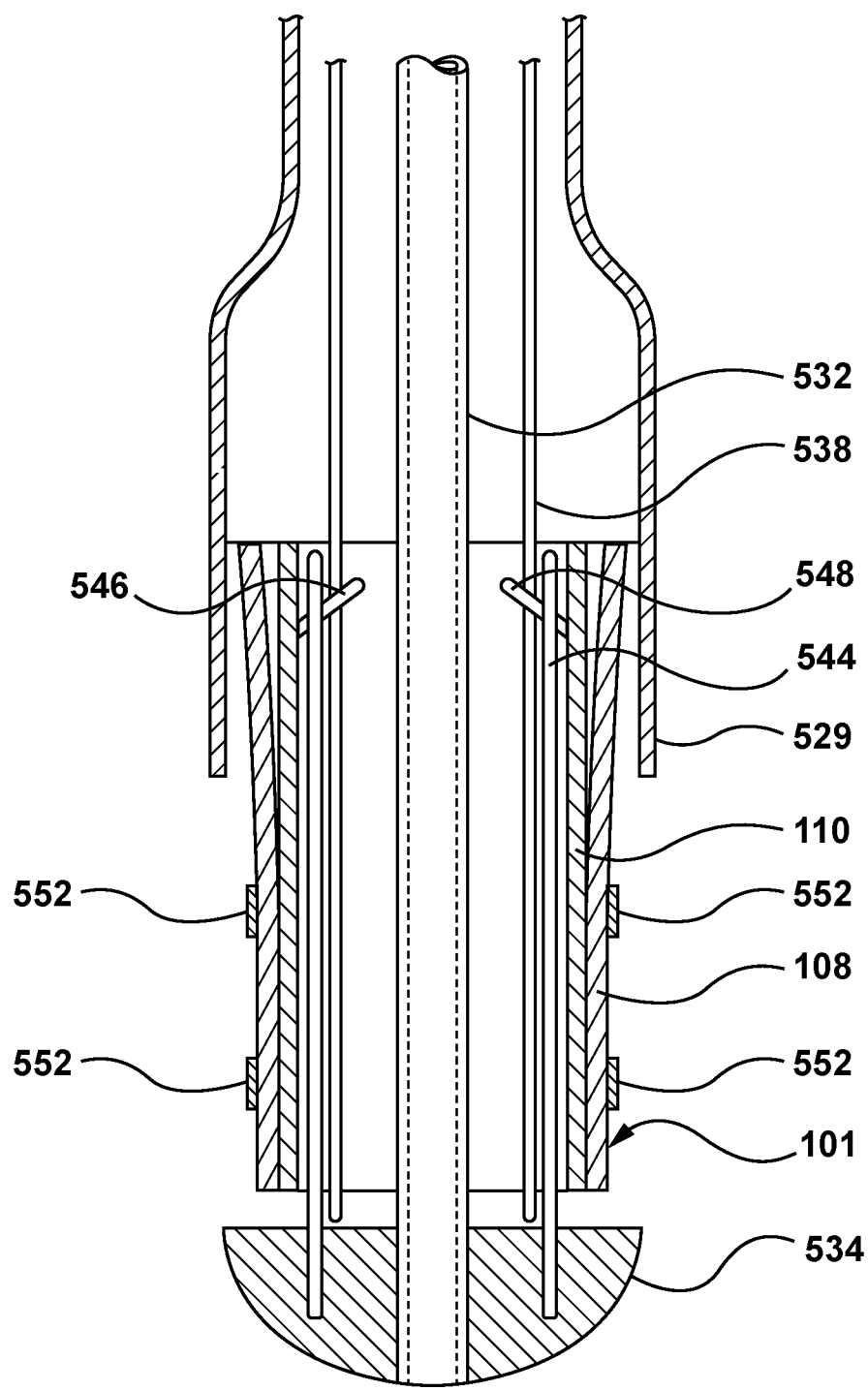
FIG. 7 is a sectional view of a distal portion of the delivery system of FIG. 5, wherein the heart valve prosthesis is shown in its reduced diameter state for delivery thereof.

In addition to being coupled to inner shaft component 532 via capsule segment 529 and cinch mechanism 550, heart valve prosthesis 101 may also be releasably coupled to inner shaft component 532 by release wires 538, as best shown in FIG. 7. FIG. 7 is an enlarged sectional view showing the distal end of delivery catheter 526 in section to illustrate the coupling of heart valve prosthesis 101 to inner shaft component 532, which is also described in more detail in U.S. Pat. No. 9,034,032 to McLean et al. previously incorporated by reference in its entirety. A plurality of locking fingers 544 are coupled to distal tip component 534 and extend proximally through the interior of valve support 110 of heart valve prosthesis 101. A selected number of posts 102 of valve support 110 of heart valve prosthesis 101 have a coupling element 548 comprising a tab 546 cut out from each post 102 at a proximal end thereof. Tab 546 may be deflected inwardly from the post 102 as shown in FIG. 7 and is configured to extend through a window or opening in locking finger 544. Release or control wires 538 pass through tabs 546, which secure heart valve prosthesis 101 to the inner shaft component 532. Release or control wires 538 can be sandwiched tightly between tabs 546 and locking fingers 544, such that friction temporarily prevents release or control wire 538 from slipping in a proximal or distal direction. In this way, capsule segment 529 may be retracted relative to heart valve prosthesis 101 to permit expansion of the first or inflow portion 118 of heart valve prosthesis 101 while inner shaft component 532 maintains the longitudinal position of heart valve prosthesis 101 relative to the anatomy. Release or control wires 538 may extend proximally to handle 542, for example, in between inner shaft component 532 and outer shaft component 528 or within one or more designated lumens. A suitable mechanism (not shown) on handle 542 can allow the operator to retract release or control wires 538 in a proximal direction until they are disengaged from tabs 546. Accordingly, heart valve prosthesis 101 can be released from locking fingers 544 and expand for deployment at the target site.

Figure 8:
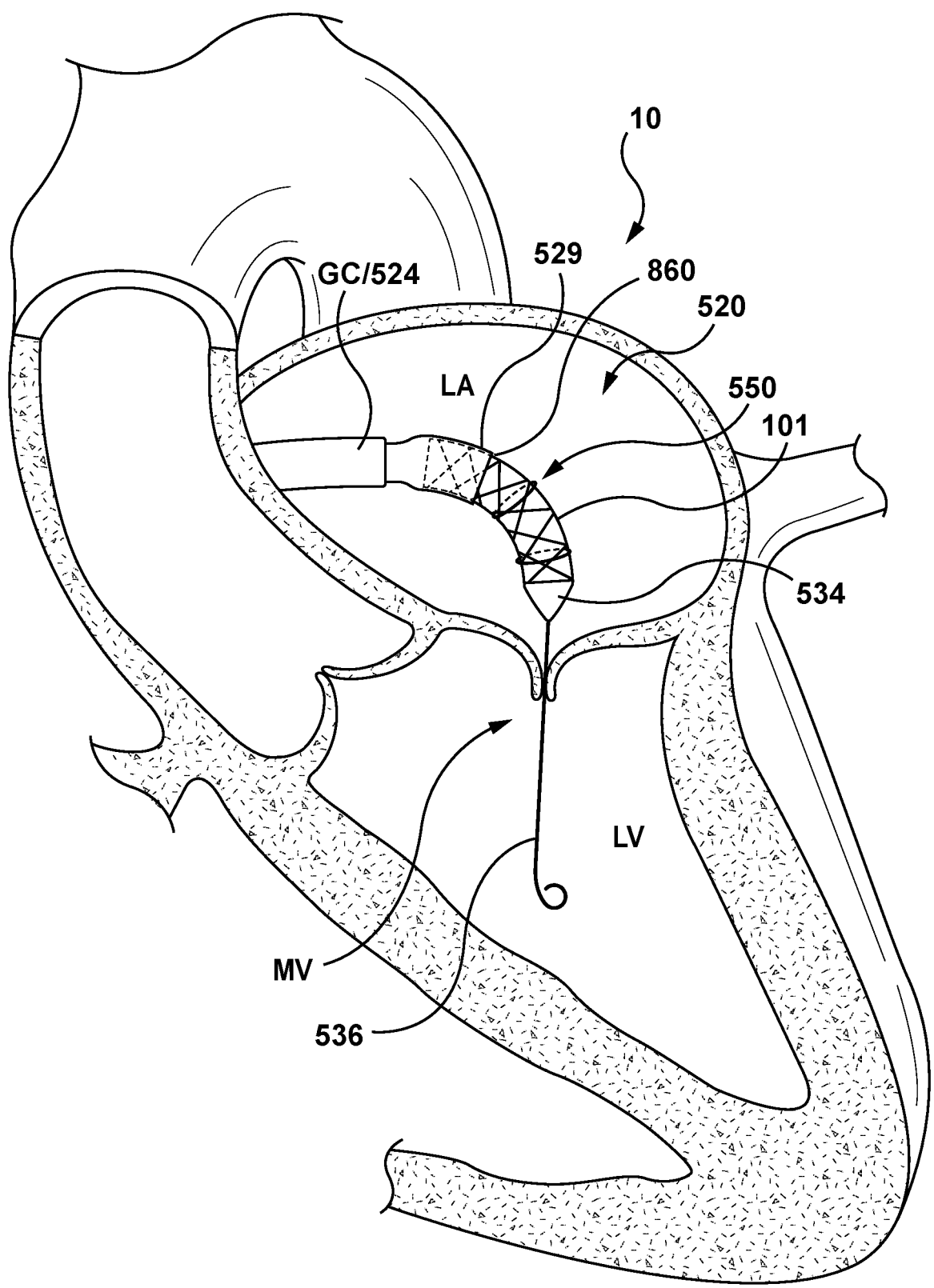
FIG. 8 is an illustration of the delivery system of FIG. 5 in situ, the delivery system being positioned into the left atrium via a transseptal approach, wherein the heart valve prosthesis is shown in its reduced diameter state for delivery thereof.

FIGS. 8-11 are sectional cut-away views of heart 10 illustrating a transseptal approach for delivering and positioning heart valve prosthesis 101 using delivery system 520 of FIG. 5 and in accordance with an embodiment hereof. With reference to FIG. 8, valve delivery system 520 is shown after having been introduced into the vasculature via a percutaneous entry point, a.k.a the Seldinger technique, and having been tracked through the vasculature and into the left atrium so that distal tip component 534 is positioned proximate the native mitral valve MV. Intravascular access to the right atrium RA may be achieved via a percutaneous access site to femoral venous access up to the inferior venal cava, or other known access routes. Thereafter, guidewire 536 is advanced through the circulatory system, eventually arriving at the heart. Guidewire 536 is directed into the right atrium, traverses the right atrium and is made to puncture with the aid of a transeptal needle or pre-existing hole, the atrial septum, thereby entering the left atrium LA. Once guidewire 536 is positioned, the endoluminal entry port and the atrial septum are dilated to permit entry of guide catheter GC into the left atrium LA. Thereafter, delivery catheter 526 is advanced over guidewire 536 and through delivery shaft 524 of guide catheter GC into the left atrium LA through the punctured atrial septum and positioned proximate or upstream to the native mitral valve MV. Although described as a transfemoral antegrade approach for percutaneously accessing the mitral valve, heart valve prosthesis 101 may be positioned within the desired area of the heart via entry other different methods such as a transseptal antegrade approach via a thoracotomy for accessing the mitral valve. In addition, although described with the use of guide catheter GC and guidewire 536, in another embodiment hereof delivery catheter 526 may access the right atrium without the use of a guidewire and/or a guide catheter.

In FIG. 8, the distal portion of delivery system 520 is shown positioned in the left atrium LA with capsule segment 529 and cinch mechanism 550 in tandem holding heart valve prosthesis 101 in a reduced diameter state. Capsule segment 529 ends proximal of cinch mechanism 550 when delivery catheter 526 is in the delivery configuration. With additional reference to FIG. 5, and as will be understood by those knowledgeable in the art, handle 542 of delivery catheter 526, as well as some length of a proximal segment of delivery catheter 526, are exposed externally of the patient for access by a clinician, even as heart valve prosthesis 101 has been advanced fully to the targeted site (e.g., left atrium LA) in the patient. By manipulating handle 542 of delivery catheter 526 from outside the vasculature, a clinician may advance and remotely manipulate and steer the distal portion of delivery catheter 526 through the sometimes tortuous intravascular path.

With capsule segment 529 and cinch mechanism 550 in tandem holding heart valve prosthesis 101 in a reduced diameter state, delivery catheter 526 is flexible enough to bend or curve the required angle when being advanced from the atrial septum towards the native mitral valve MV. More particularly, during a transseptal approach, the distal portion of delivery catheter 526 is required to bend or curve approximately 90 degrees in order to be positioned proximate to the native mitral valve MV. The relatively short capsule segment 529 essentially forms a hinge point 860 at which the distal portion of delivery catheter 526 is allowed to bend or turn within the confined space of the left atrium LA. Hinge point 860 is distal to a distal end of capsule segment 529. Thus, delivery catheter 526 having the relatively short capsule segment 529 is permitted to turn or bend more flexibility than a delivery catheter with a long, rigid capsule covering the full length of the heart valve prosthesis.

Figure 9:
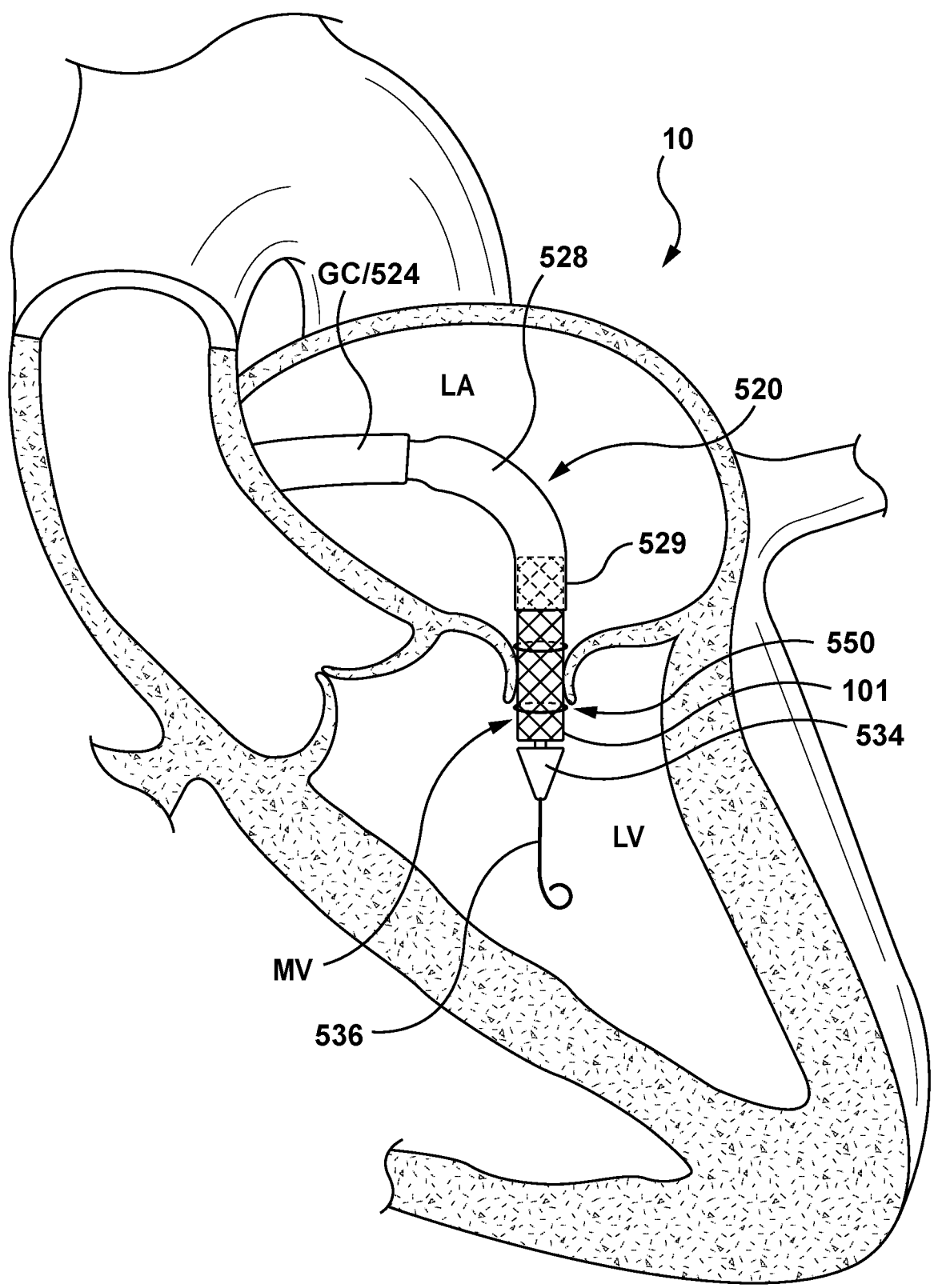
FIG. 9 is an illustration of the delivery system of FIG. 5 in situ, wherein the heart valve prosthesis is shown in its reduced diameter state for delivery thereof and positioned within an annulus of a native mitral valve.
Figure 10:
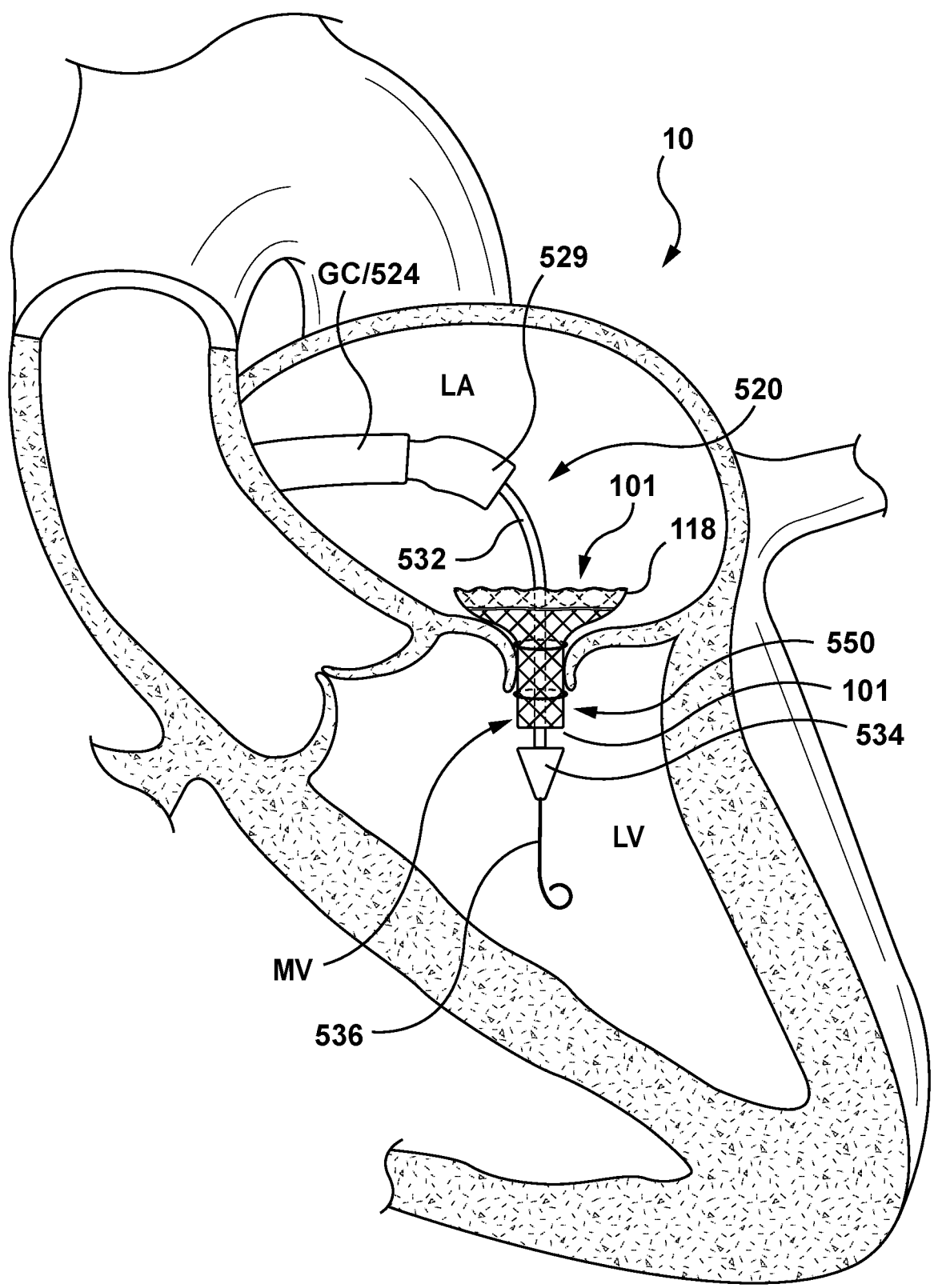
FIG. 10 is an illustration of the delivery system of FIG. 5 in situ, wherein a first stage of deployment of the heart valve prosthesis is shown in which the capsule segment of the delivery system has been proximally retracted to deploy an inflow end of the heart valve prosthesis.

In a next delivery step shown in FIG. 9, delivery catheter 526 is advanced into proximity to and/or apposition within the annulus and/or leaflets of native mitral valve MV. Distal tip component 534 is advanced into the left ventricle LV until heart valve prosthesis 101 in the reduced diameter state is centered at the native mitral valve. At this stage of delivery, capsule segment 529 and cinch mechanism 550 in tandem are still holding heart valve prosthesis 101 in a reduced diameter state.

Once heart valve prosthesis 101 is positioned within the mitral valve MV, handle 542 (not shown in FIGS. 8-11) is actuated such that outer shaft component 528 is retracted in a proximal direction such that capsule segment 529 is longitudinally repositioned (proximally retracted in this embodiment) and the first or inflow portion 118 of heart valve prosthesis 101 (which includes at least brim 112 of heart valve prosthesis 101) is no longer retained within the capsule segment. Capsule segment 529 is proximally retracted to expose and release the first or inflow portion 118 of heart valve prosthesis 101, and thereby to permit the first or inflow portion 118 of heart valve prosthesis 101 to return to an expanded state within an atrial area of the native mitral valve MV. When the first or inflow portion 118 of heart valve prosthesis 101 deploys, at least brim 112 of heart valve prosthesis 101 radially expands. In addition to brim 112, an inflow end of valve support 110 and/or anchoring member 108 may also partially radially expand in order to permit full radial expansion of brim 112. Retraction of capsule segment 529 and subsequent deployment of the first or inflow portion 118 of heart valve prosthesis 101 may be considered a first stage of deployment of a two-stage deployment process for heart valve prosthesis 101. After proximal retraction of capsule segment 529, cinch mechanism 550 maintains the second portion or outflow portion 116 of heart valve prosthesis 101 (which includes anchoring member 108 and valve support 110) in the reduced diameter state.

Figure 11:
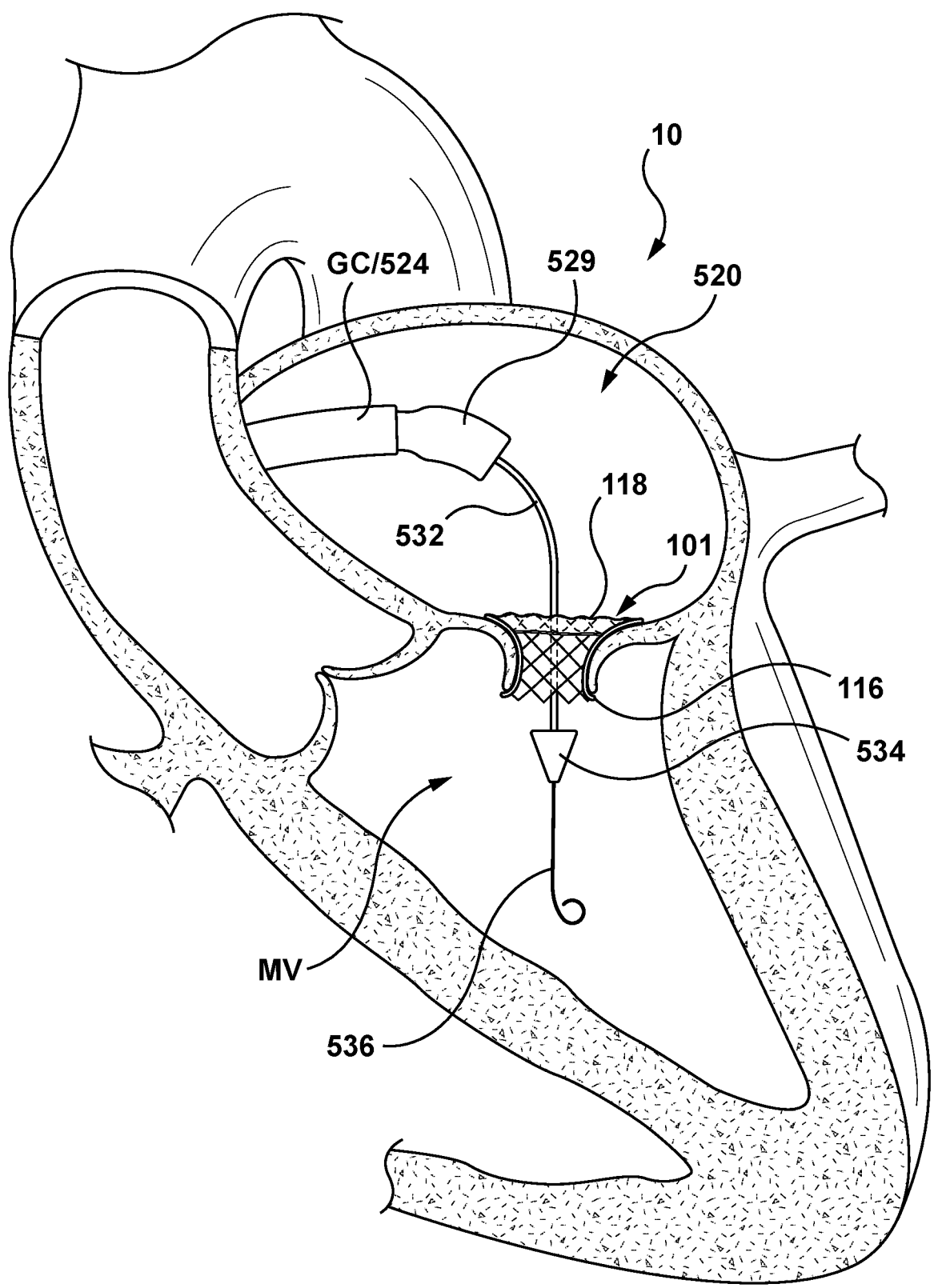
FIG. 11 is an illustration of the delivery system of FIG. 5 in situ, wherein a second stage of deployment of the heart valve prosthesis is shown in which the cinch mechanism of the delivery system has been released to deploy an outflow end of the heart valve prosthesis.

With reference to FIG. 11, heart valve prosthesis 101 is then fully deployed or expanded into apposition with the annulus of the native mitral valve. FIG. 11 is an illustration of a second stage of deployment of heart valve prosthesis 101 in which cinch mechanism 550 has been released to deploy the second portion of outflow portion 116 of heart valve prosthesis 101. Cinch mechanism 550 is released to permit the second portion of outflow portion 116 of heart valve prosthesis 101 to return to an expanded state within an annulus of the native mitral valve MV. When the second or outflow portion 116 of heart valve prosthesis 101 deploys, anchoring member 108 and valve support 110 of heart valve prosthesis 101 radially expands. Actuation of cinch mechanism 550 as previously described with respect to FIG. 6 provides slack or releases suture(s) 552 thereby allowing the second portion of outflow portion 116 of heart valve prosthesis 101 to self-expand to the expanded configuration into apposition with the surrounding native anatomy, i.e., with the annulus of the native mitral valve MV.

After full deployment of heart valve prosthesis 101, release or control wires 538 may be retracted in a proximal direction to release heart valve prosthesis 101 from delivery catheter 526, allowing delivery system 520 to be removed and heart valve prosthesis 101 to be fully implanted at the native mitral valve in the expanded configuration. Following delivery, placement and implantation of heart valve prosthesis 101 within the mitral valve MV (or other desired valve location), delivery system 520 is removed from the heart and out of the body of the patient, as would be understood by one of skill in the art. In an embodiment, heart valve prosthesis 101 may be expanded upstream of the desired target location then pulled downstream into the target location before releasing heart valve prosthesis 101 from delivery catheter 526. Alternatively, heart valve prosthesis 101 may not be connected to the delivery catheter such that heart valve prosthesis 101 deploys and is fully released from delivery catheter 526 after proximal retraction of capsule segment 529 and release of cinch mechanism 550.

Image guidance, e.g., intracardiac echocardiography (ICE), fluoroscopy, computed tomography (CT), intravascular ultrasound (IVUS), optical coherence tomography (OCT), or another suitable guidance modality, or combination thereof, may be used to aid the clinician's delivery and positioning of heart valve prosthesis 101 at the target native valve region. In another embodiment, selected outer surfaces of the distal portion of delivery catheter 526 may be treated such that the echogenicity thereof is enhanced. In some embodiments, image guidance components (e.g., IVUS, OCT) may be coupled to delivery catheter 526 to provide three-dimensional images of the vasculature proximate to the target heart valve region to facilitate positioning, orienting and/or deployment of heart valve prosthesis 101 within the heart valve region.

Although FIGS. 8-11 illustrate a mitral valve replacement, delivery system 520 in which capsule segment 529 and cinch mechanism 550 in tandem hold heart valve prosthesis 101 in a reduced diameter state may be utilized for delivering other valve prostheses for replacement of the respective native valve such as but not limited to an aortic valve prosthesis. In addition, although the two-stage deployment process is illustrated in FIGS. 8-11 with deployment of inflow portion 118 of heart valve prosthesis 101 deployed via capsule segment 529 prior to deployment of outflow portion 116 of heart valve prosthesis 101 deployed via release of cinch mechanism 550, in another embodiment hereof the cinch mechanism may be released prior to retraction of the capsule segment such that the outflow portion 116 of heart valve prosthesis 101 is deployed prior to the inflow portion 118 of heart valve prosthesis 101. The order or sequence of the two-stage deployment is dependent upon a patient's anatomy and application, for example depending upon which valve is being replaced (i.e., mitral, aortic, tricuspid, or pulmonary valve) and the configuration of the heart valve prosthesis.

Figure 12:
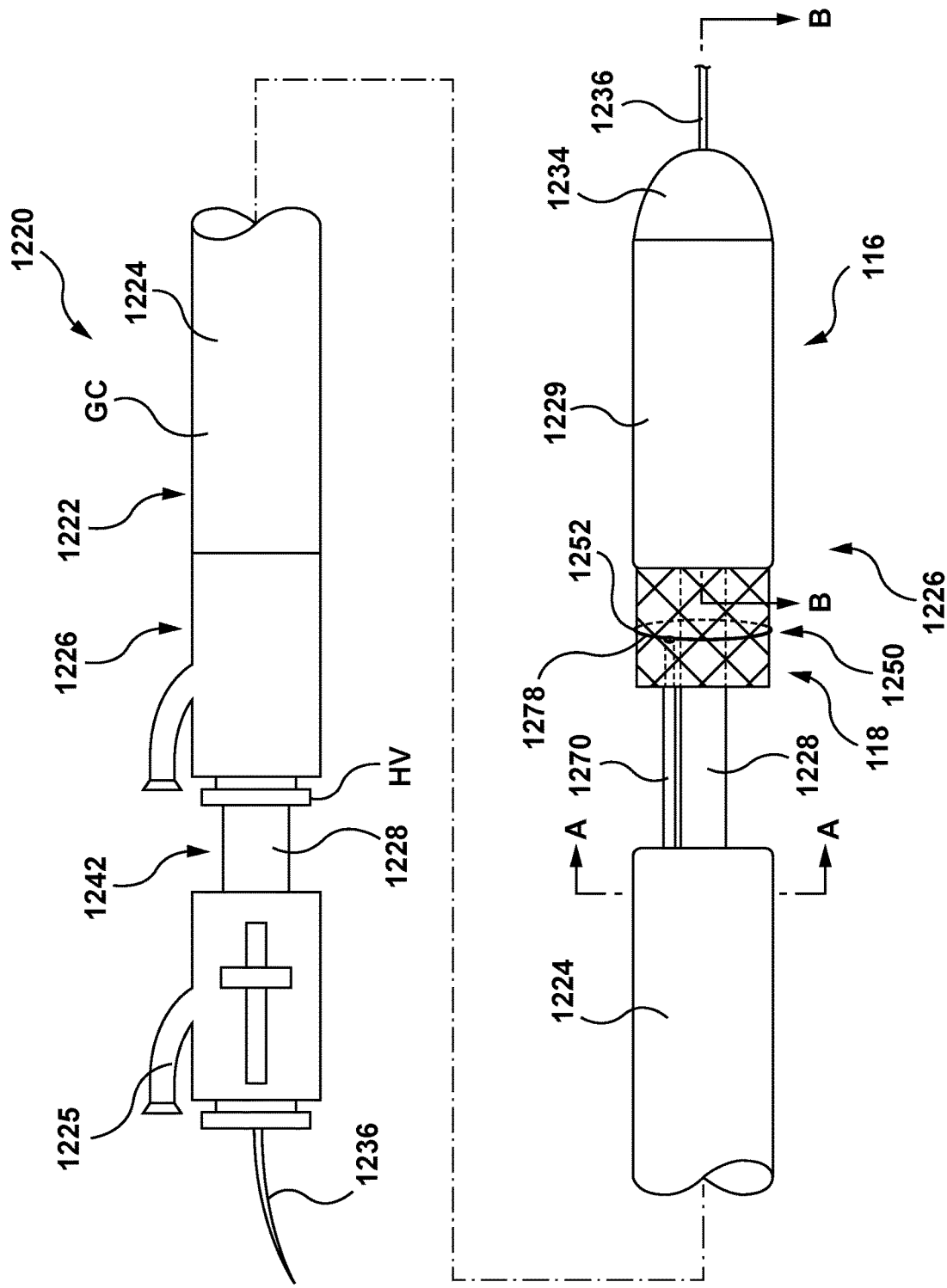
FIG. 12 is a side view illustration of a delivery system configured to deliver the heart valve prosthesis of FIG. 3A according to another embodiment hereof, wherein the delivery system includes a capsule segment and a cinch mechanism that are configured in tandem to hold the heart valve prosthesis in a reduced diameter state and the heart valve prosthesis is shown in its reduced diameter state for delivery thereof.
Figure 12A:
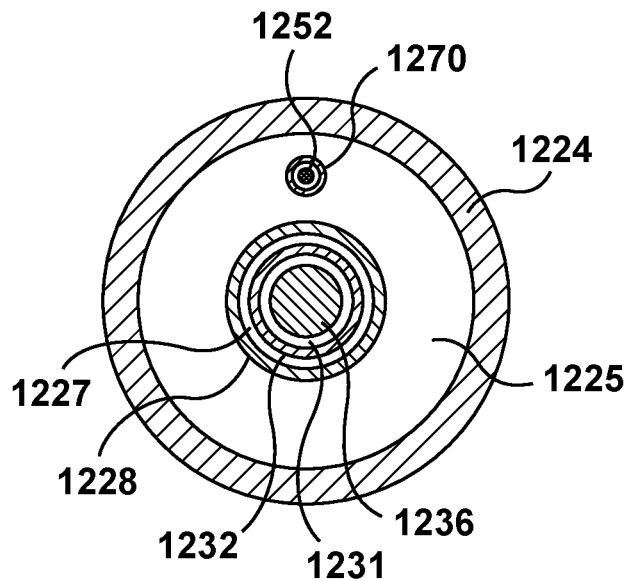
FIG. 12A is a cross-sectional view taken along line A-A of FIG. 12.
Figure 12B:
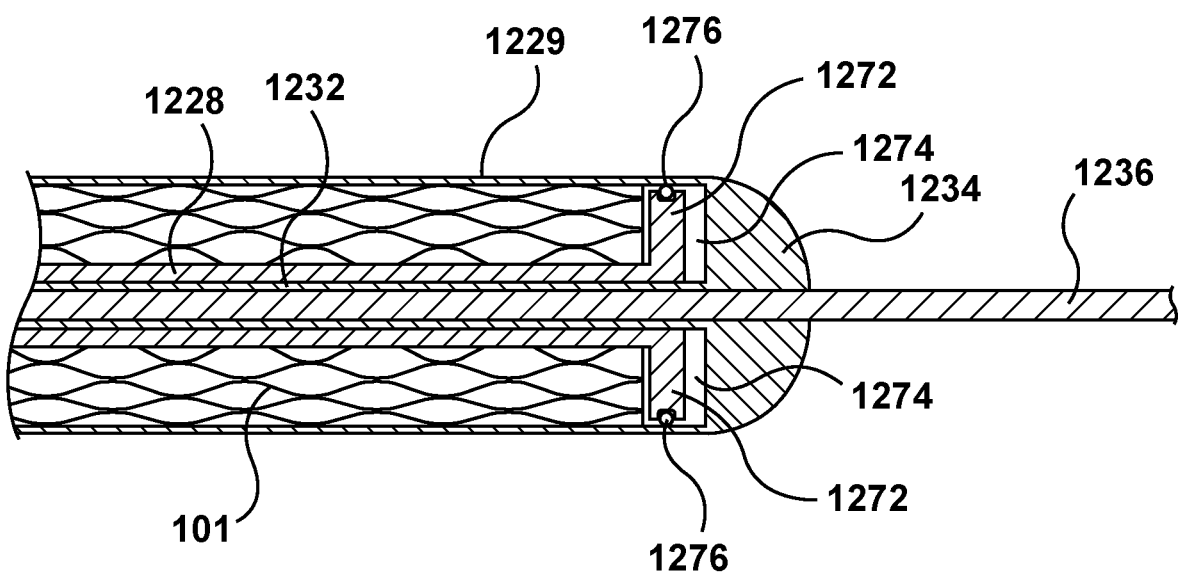
FIG. 12B is a cross-sectional view taken along line B-B of FIG. 12.

In another embodiment hereof, inflow portion 118 of heart valve prosthesis 101 may be deployed via a cinch mechanism and outflow portion 116 of heart valve prosthesis 101 may be deployed via a capsule segment. More particularly, FIG. 12 is a side view illustration of a delivery system 1220 according to an embodiment hereof which may be used to deliver and deploy heart valve prosthesis 101 disclosed herein to the heart of a patient. FIG. 12A is a cross-sectional view taken along line A-A of FIG. 12, and FIG. 12B is a sectional view taken along line B-B of FIG. 12. Similar to delivery system 520, delivery system 1220 includes guiding catheter GC (described above with respect to delivery system 520) and a delivery catheter 1226 placed through a hemostasis valve HV on the proximal end of guiding catheter GC. Guiding catheter GC includes a delivery shaft 1224, which is similar to delivery shaft 524. As will be described in more detail herein, delivery system 1220 includes a capsule segment 1229 and a cinch mechanism 1250 that are configured in tandem to hold heart valve prosthesis 101 in a reduced diameter state. Capsule segment 1229 and cinch mechanism 1250 are disposed longitudinally adjacent to each other and do not overlap when delivery catheter 1226 is in a delivery configuration. As used in this embodiment, "do not overlap" means that capsule segment 1229 does not cover the first or inflow portion 118 of heart valve prosthesis 101 when delivery catheter 1226 is in a delivery configuration and cinch mechanism 1250 does not hold or retain the second or outflow portion 116 of heart valve prosthesis 101 in a reduced diameter state for delivery when delivery catheter 1226 is in a delivery configuration. Capsule segment 1220 is relatively short (i.e., has a length less than the length of heart valve prosthesis 101 in its reduced diameter state) and is configured to hold only outflow portion 116 of heart valve prosthesis 101 in a reduced diameter state for delivery and proximal portion 118 of heart valve prosthesis 101 is held in a reduced diameter state by cinch mechanism 1250.

Delivery catheter 1226 is depicted in a delivery configuration in FIG. 12 with heart valve prosthesis 101 loaded within capsule segment 1229 of the delivery system. As best shown in FIG. 12A, delivery catheter 1226 includes a first tubular shaft or outer shaft component 1228 defining a lumen 1227 therethrough and a second tubular shaft or inner shaft component 1232 defining a lumen 1231 therethrough. Inner shaft component 1232 is concentrically slidably disposed within lumen 1227 of outer shaft component 1228. Lumen 1231 of inner shaft component 1232 may be sized to slidingly receive a guidewire 1236 such that delivery catheter 1226 may be tracked over the guidewire during delivery of heart valve prosthesis 101. Stated another way, a guidewire lumen of delivery catheter 1226 is defined by inner shaft component 1232 and a distal tip component 1234.

In the embodiment of FIG. 12, as best shown in the sectional view of FIG. 12B, capsule segment 1229 is concentrically disposed over a distal portion of outer shaft component. Nosecone or distal tip component 1234 is attached to a distal end of capsule segment 1229, thereby defining a blind annular cavity 1274. A piston 1272 is slideably disposed in cavity 1274 and has an O-ring 1276 around its circumference to create a fluid seal with the wall of cavity 1274. Outer shaft component 1228 extends proximally from piston 1272 and is slideably mounted over inner shaft component 1232. Lumen 1227, which is annular and defined between outer shaft component 1228 and inner shaft component 1232, is in fluid communication with cavity 1274 and functions for delivery of a fluid to hydraulically actuate piston 1272.

Capsule segment 1229 functions to protect, secure, and compressively retain a first portion of heart valve prosthesis 101 for delivery. More particularly, capsule segment 1229 is configured to encircle a first portion of heart valve prosthesis 101 and to thereby hold or compressively retain the first portion of heart valve prosthesis 101 in a reduced diameter state for delivery to a treatment site. In in this embodiment, the first portion is outflow portion 116 of heart valve prosthesis 101 (shown on FIGS. 3 and 4) and includes anchoring member 108 and valve support 110 of heart valve prosthesis 101. Stated another way, outflow portion 116 of heart valve prosthesis 101 is retained within cavity 1274, with outer shaft component 1228 and inner shaft component 1232 extending through the interior thereof. Capsule segment 1229 is configured to be distally advanced relative to inner shaft component 1232 to release and deploy anchoring member 108 and valve support 110 of heart valve prosthesis 101 from capsule segment 1229. More particularly, in order to be distally advanced relative to inner shaft component 1232, capsule segment 1229 is coupled to outer shaft component 1228 so as to be moveable therewith. Fluid is injected through lumen 1227 into cavity 1274, distal to piston 1272, in order to drive capsule segment 1229 distally. Delivery catheter 1226 and heart valve prosthesis 101 may remain in a stationary longitudinal position relative to the native valve while heart valve prosthesis 101 is deployed, thereby increasing the precision of deployment. In addition, such hydraulic actuation allows capsule segment 1229 to be moved in incremental steps to only partially deploy heart valve prosthesis 101, allowing the operator to assess its position relative to the native valve and reposition as needed before complete deployment. In this embodiment, piston 1272 is hydraulically actuated, however, in another embodiment, piston 1272 may be operated by manual distal advancement of outer shaft component 1232 and capsule segment 1229 coupled thereto. In such an embodiment, delivery catheter 1226 may be equipped with a retraction mechanism on a handle 1242 of delivery catheter 1226.

A second portion of heart valve prosthesis 101 is disposed proximal to a proximal end of capsule segment 1229. In an embodiment hereof, the second portion includes inflow portion 118 of heart valve prosthesis 101 (shown on FIGS. 3 and 4) and includes brim 112 of heart valve prosthesis 101. Cinch mechanism 1250 surrounds or encircles the second portion of heart valve prosthesis 101 and is configured to hold the remainder of the heart valve prosthesis (i.e., the remaining length of heart valve prosthesis 101 proximal to capsule segment 1229) in a reduced diameter state for delivery to the treatment site. Due to cinch mechanism 1250, delivery catheter 1226 beneficially does not include or require a long retractable capsule for compressing the second or inflow portion 118 of heart valve prosthesis 101, and therefore may be more efficiently utilized within the confines of native anatomy having small or restricted space such as but not limited to the left atrium and/or the left ventricle. Thus, capsule segment 1229 compressively holds or retains the first or outflow portion 116 of heart valve prosthesis 101 in a reduced diameter state for delivery, while cinch mechanism 1250 compressive holds or retains the second or inflow portion 118 of heart valve prosthesis 101 in a reduced diameter state for delivery. Delivery catheter 1226 permits a two-stage deployment of heart valve prosthesis 101 because capsule segment 1229 is configured to be distally advanced relative to inner shaft component 532 to permit the first or outflow portion 116 of heart valve prosthesis 101 to return to an expanded or deployed state and cinch mechanism 1250 is releasable to permit the second or inflow portion 118 of heart valve prosthesis 101 to return to an expanded or deployed state as will be described in more detail herein with respect to FIGS. 18-21.

Cinching mechanism 1250 will now be described in more detail with additional reference to FIGS. 13-15. In the embodiment of FIG. 12, a suture tube or shaft 1270 extends through an annular lumen 1225 that is defined between delivery shaft 1224 of guiding catheter GC and outer shaft component 1228. A suture 1252 extends through suture tube or shaft 1270. Suture 1252 extends to a proximal end of delivery catheter 1226 and is releasable to permit the second or inflow portion 118 of heart valve prosthesis 101 to return to an expanded or deployed state. More particularly, suture 1252 is disposed about the second or inflow portion 118 of heart valve prosthesis 101 such that pulling suture 1252 controls constriction/compression of the second or inflow portion 118 of heart valve prosthesis 101 and releasing/removing suture 1252 controls expansion/deployment of the second or inflow portion 118 of heart valve prosthesis 101. Suture 1252 includes or forms a loop 1278 that encircles or extends circumferentially around an outer surface of the second or inflow portion 118 of heart valve prosthesis 101, such that suture 1252 constrains the second or inflow portion 118 of heart valve prosthesis 101 in the reduced diameter state, releasably coupling the second or inflow portion 118 of heart valve prosthesis 101 to inner shaft component 1232. In an embodiment, suture 1252 may be formed from a monofilament or plastic suture material, such as polypropylene.

Figure 13:
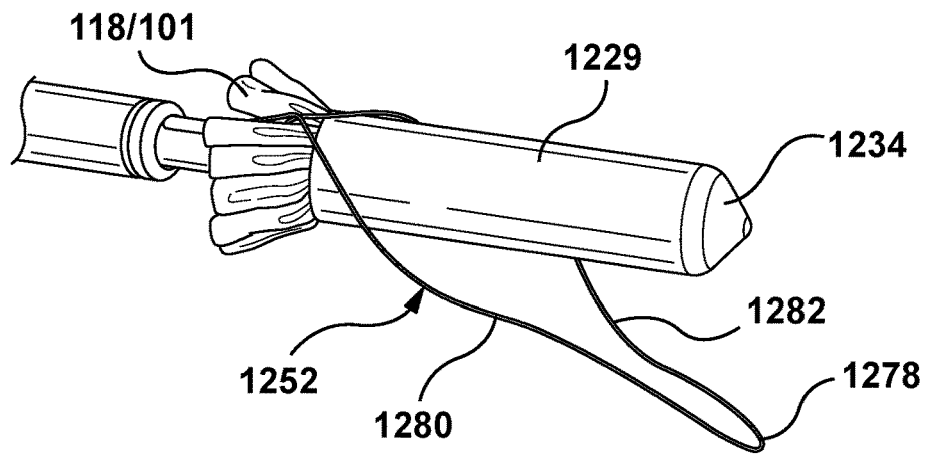
FIG. 13 is a perspective illustration of positioning a suture loop onto an inflow portion of the heart valve prosthesis loaded into the delivery system of FIG. 12, wherein the suture loop is positioned distal of a distal tip component of the delivery system of FIG. 12.
Figure 14:
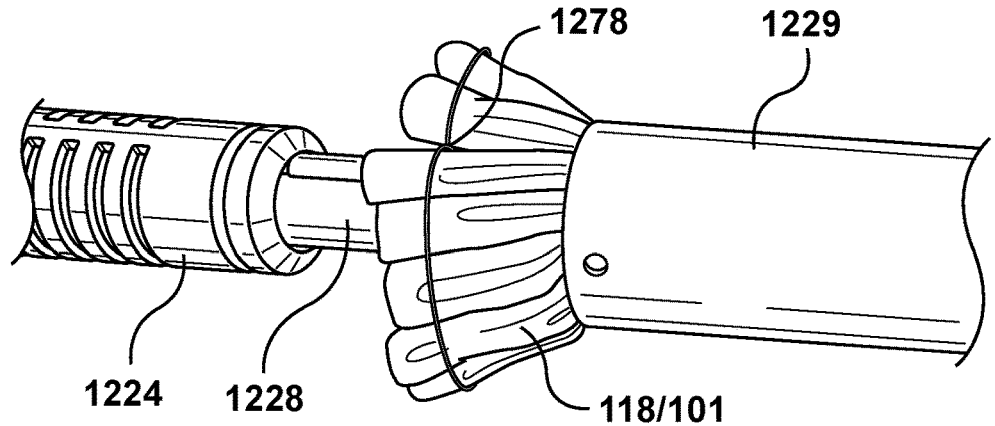
FIG. 14 is a perspective illustration of positioning a suture loop onto the heart valve prosthesis loaded into the delivery system of FIG. 12, wherein the suture loop is positioned loosely over the inflow portion of the heart valve prosthesis.
Figure 15:
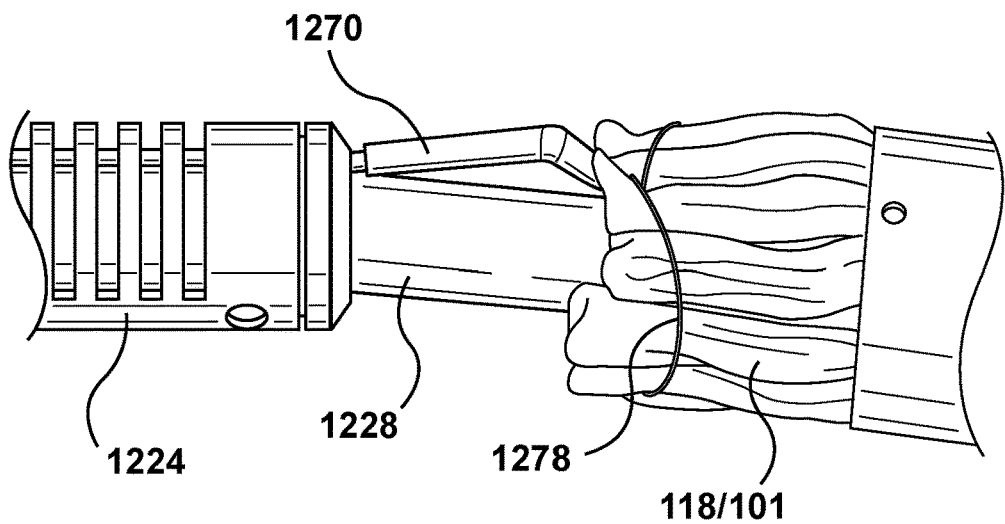
FIG. 15 is a perspective illustration of positioning a suture loop onto the heart valve prosthesis loaded into the delivery system of FIG. 12, wherein the suture loop is positioned tightly or cinched over the inflow portion of the heart valve prosthesis.

FIGS. 13-15 illustrate a method of positioning loop 1278 of suture 1252 around the second or inflow portion 118 of heart valve prosthesis 101. Suture 1252 and loop 1278 are pre-loaded into suture tube 1270 and delivery system 1220. Heart valve prosthesis 101 is loaded into capsule segment 1229 with inflow portion 118 of heart valve prosthesis 101, including at least brim 112 of heart valve prosthesis 101, exposed or proximally extending from a proximal end of capsule segment 1229. In an embodiment hereof, inflow portion 118 of heart valve prosthesis 101 that is exposed or proximally extending from a proximal end of capsule segment 1229 has a length of approximately 15 mm. As shown FIG. 13, loop 1278 of suture 1252 is positioned distal of a distal end of suture tube 1270. Slack or additional length of suture 1252 initially extends distally from the distal end of suture tube 1270 such that loop 1278 of suture 1252 is distal of distal tip component 1234. Loop 1278 of suture 1252 is positioned or oriented substantially parallel to capsule segment 1229 so that a first leg 1280 of loop 1278 is positioned on a first side of capsule segment 1229 and an opposing or second leg 1282 of loop 1278 is positioned on a second or opposing side of capsule segment 1229, as shown in FIG. 13. As shown in FIG. 14, tension is then applied to a proximal end of suture 1252 (not shown; extending proximally from handle 1242 of delivery catheter 1226) in order to retract slack of suture 1252 into suture tube 1270 and position loop 1278 loosely over inflow portion 118 of heart valve prosthesis 101, which includes at least brim 112 of heart valve prosthesis 101 as previously described. Tension is further applied to the proximal end of suture 1252 in order to cinch loop 1278 and inflow portion 118 of heart valve prosthesis 101 tightly around outer shaft component 1228 of delivery catheter 1226 as shown in FIG. 15. In this embodiment, positioning of suture 1252 is simplified since suture 1252 is an integral component of delivery system 1220 that is pre-loaded into suture tube 1270 as part of the original manufacturing of delivery system 1220.

Figure 16:
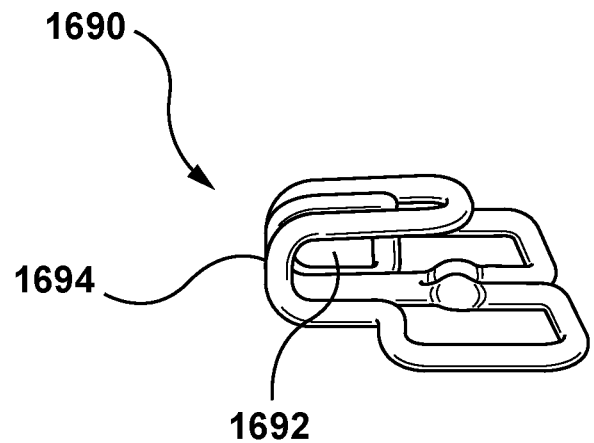
FIG. 16 is a perspective view of a clip or clasp that may be utilized in positioning a suture loop onto the heart valve prosthesis loaded into the delivery system of FIG. 12 in order to prevent the suture loop from slipping off the inflow portion of the heart valve prosthesis during tightening.

FIG. 16 illustrate a perspective view of a clip or clasp 1690 that may be utilized in positioning loop 1278 of suture 1252 around the second or inflow portion 118 of heart valve prosthesis 101 in order to prevent loop 1278 from slipping off the second or inflow portion 118 of heart valve prosthesis 101 during tightening. A plurality of clips 1690 may be sewn or otherwise attached to the second or inflow portion 118 of heart valve prosthesis 101, approximately equally circumferentially spaced apart around the outer surface of the second or inflow portion 118 of heart valve prosthesis 101. In an embodiment, the plurality of clips 1690 may be sewn or otherwise attached to the proximal edge of the second or inflow portion 118 of heart valve prosthesis 101. When loop 1278 of suture 1252 is being tightened and cinched around the second or inflow portion 118 of heart valve prosthesis 101, loop 1278 is received and secured within each clasp 1690 via an open end 1692 of each clasp 1690. When loop 1278 is positioned within each clasp 1690, loop 1278 abuts against a closed end or stop 1264 of each clasp 1690 and thus cannot slip or slide off heart valve prosthesis 101 during tightening.

Figure 17:
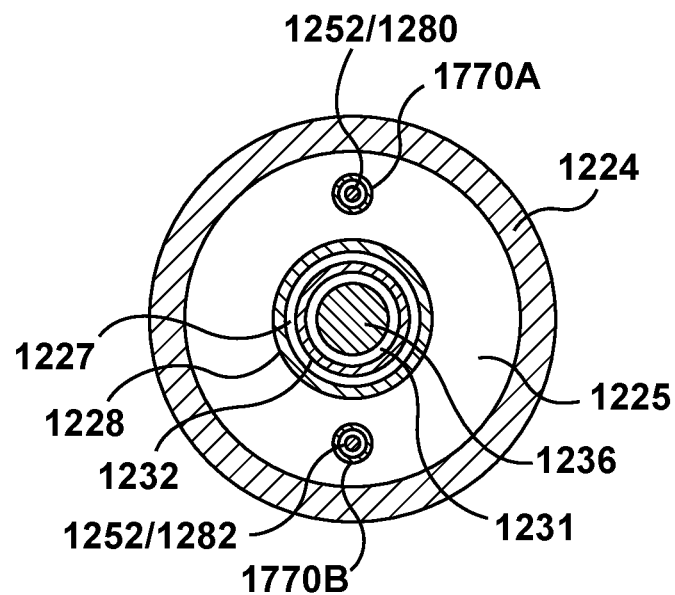
FIG. 17 is a cross-sectional view taken along line A-A of FIG. 12 according to another embodiment hereof, wherein the delivery system includes two suture tubes for pre-loading the suture therein.

In another embodiment hereof, delivery system 1220 may include two suture tubes 1770A, 1770B for pre-loading suture 1252 therein. As shown in FIG. 17, which is a cross-sectional view similar to FIG. 12A, suture tubes 1770A, 1770B extend through annular lumen 1225 that is defined between delivery shaft 1224 of guiding catheter GC and outer shaft component 1228. Suture tubes 1770A, 1770B are spaced approximately 180 degrees apart within annular lumen 1225. Suture 1252 extends through suture tubes 1770A, 1770B, with first leg 1280 of suture 1252 being disposed within suture tube 1770A and second leg 1282 of suture 1252 being disposed within suture tube 1770B, with loop 1278 (not shown in FIG. 17) being positioned around outer shaft component 1228. Loop 1278 is initially sufficiently large enough in diameter in order to be positioned over the second or inflow portion 118 of heart valve prosthesis 101, and then loop 1278 is tightened and cinched around the second or inflow portion 118 of heart valve prosthesis 101 by applying tension to a proximal end of suture 1252 as described above. In this embodiment, due to opposing suture tubes 1770A, 1770B, loop 1278 may remain approximately perpendicular to outer shaft component 1228 during the positioning process.

Figure 18:
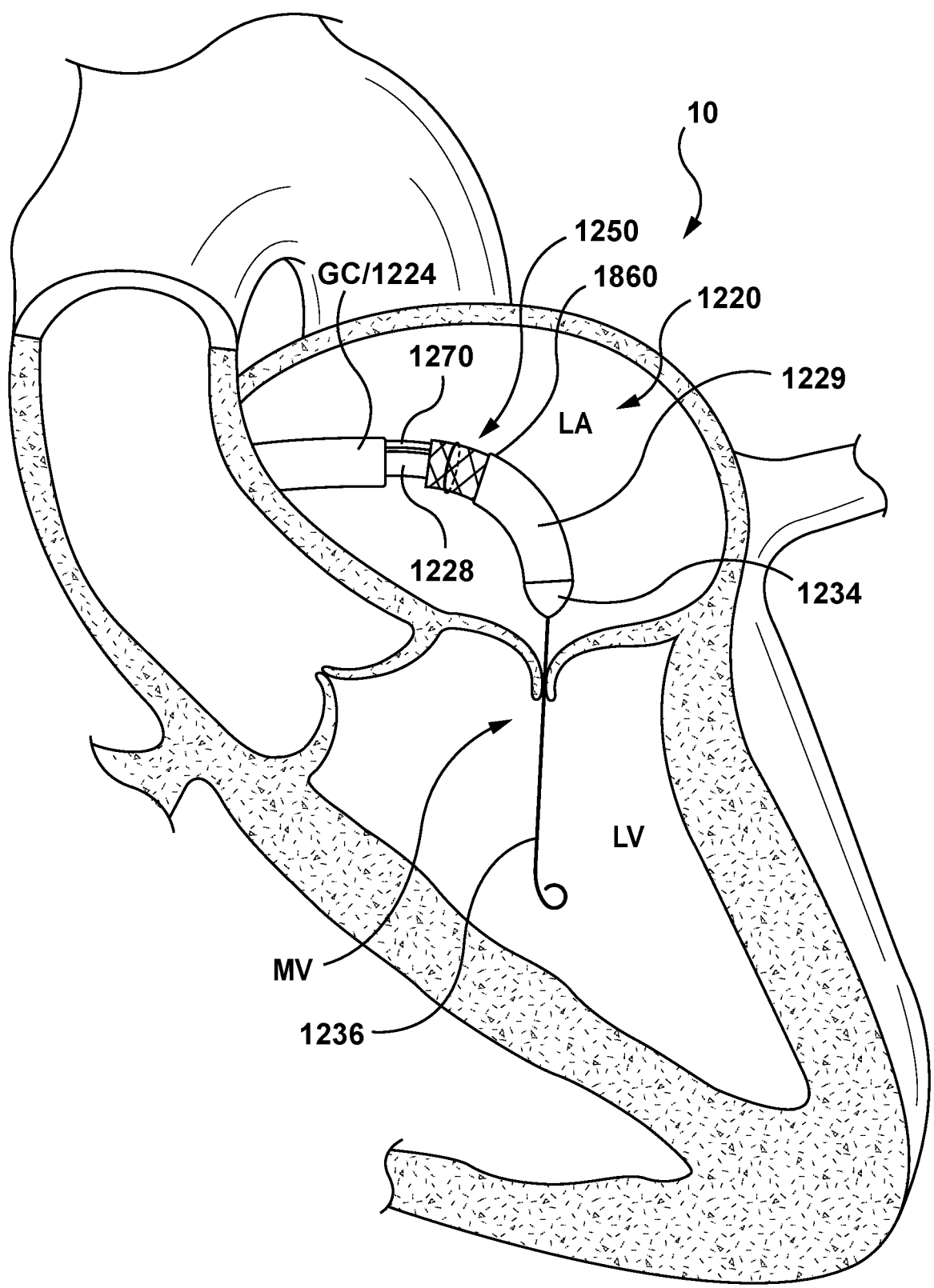
FIG. 18 is an illustration of the delivery system of FIG. 12 in situ, the delivery system being positioned into the left atrium via a transseptal approach, wherein the heart valve prosthesis is shown in its reduced diameter state for delivery thereof.

FIGS. 18-21 are sectional cut-away views of heart 10 illustrating a transseptal approach for delivering and positioning heart valve prosthesis 101 using delivery system 1220 of FIG. 12 and in accordance with an embodiment hereof. With reference to FIG. 18, valve delivery system 1220 is shown after having been introduced into the vasculature via a percutaneous entry point, a.k.a the Seldinger technique, and having been tracked through the vasculature and into the left atrium so that distal tip component 1234 is positioned proximate the native mitral valve MV. Intravascular access to the right atrium RA may be achieved via a percutaneous access site to femoral venous access up to the inferior venal cava, or other known access routes. Thereafter, guidewire 1236 is advanced through the circulatory system, eventually arriving at the heart. Guidewire 1236 is directed into the right atrium, traverses the right atrium and is made to puncture with the aid of a transeptal needle or pre-existing hole, the atrial septum, thereby entering the left atrium LA. Once guidewire 1236 is positioned, the endoluminal entry port and the atrial septum are dilated to permit entry of guide catheter GC into the left atrium LA. Thereafter, delivery catheter 1226 is advanced over guidewire 1236 and through delivery shaft 1224 of guide catheter GC into the left atrium LA through the punctured atrial septum and positioned proximate or upstream to the native mitral valve MV. Although described as a transfemoral antegrade approach for percutaneously accessing the mitral valve, heart valve prosthesis 101 may be positioned within the desired area of the heart via entry other different methods such as a transseptal antegrade approach via a thoracotomy for accessing the mitral valve. In addition, although described with the use of guide catheter GC and guidewire 1236, in another embodiment hereof delivery catheter 1226 may access the right atrium without the use of a guidewire and/or a guide catheter.

In FIG. 18, the distal portion of delivery system 1220 is shown positioned in the left atrium LA with capsule segment 1229 and cinch mechanism 1250 in tandem holding heart valve prosthesis 101 in a reduced diameter state. Cinch mechanism 1250 ends proximal of capsule segment 1229 when delivery catheter 1226 is in the delivery configuration. With additional reference to FIG. 12, and as will be understood by those knowledgeable in the art, handle 1242 of delivery catheter 1226, as well as some length of a proximal segment of delivery catheter 1226, are exposed externally of the patient for access by a clinician, even as heart valve prosthesis 101 has been advanced fully to the targeted site (e.g., left atrium LA) in the patient. By manipulating handle 1242 of delivery catheter 1226 from outside the vasculature, a clinician may advance and remotely manipulate and steer the distal portion of delivery catheter 1226 through the sometimes tortuous intravascular path.

With capsule segment 1229 and cinch mechanism 1250 in tandem holding heart valve prosthesis 101 in a reduced diameter state, delivery catheter 1226 is flexible enough to bend or curve the required angle when being advanced from the atrial septum towards the native mitral valve MV. More particularly, during a transseptal approach, the distal portion of delivery catheter 1226 is required to bend or curve approximately 90 degrees in order to be positioned proximate to the native mitral valve MV. The relatively short capsule segment 1229 essentially forms a hinge point 1860 at which the distal portion of delivery catheter 1226 is allowed to bend or turn within the confined space of the left atrium LA. Hinge point 1860 is proximal to a proximal end of capsule segment 1229. Thus, delivery catheter 1226 having the relatively short capsule segment 1229 is permitted to turn or bend more flexibility than a delivery catheter with a long, rigid capsule covering the full length of the heart valve prosthesis.

Figure 19:
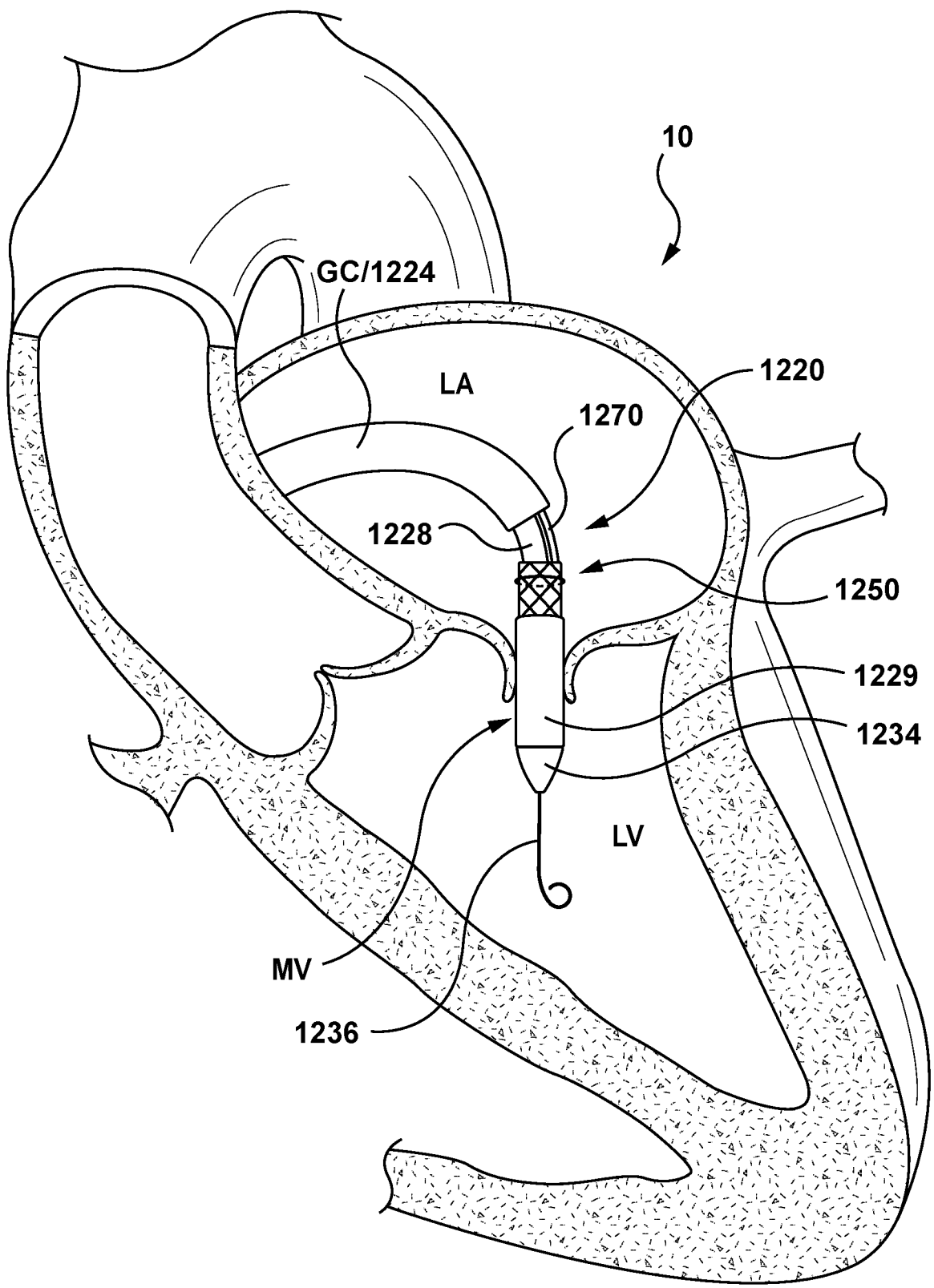
FIG. 19 is an illustration of the delivery system of FIG. 12 in situ, wherein the heart valve prosthesis is shown in its reduced diameter state for delivery thereof and positioned within an annulus of a native mitral valve.

In a next delivery step shown in FIG. 19, delivery catheter 1226 is advanced into proximity to and/or apposition within the annulus and/or leaflets of native mitral valve MV. More particularly, delivery shaft 1224 of guide catheter GC and delivery catheter 1226 are simultaneously distally advanced in order to position heart valve prosthesis 101 as desired, with suture tube 1270 extending alongside outer shaft component 128 within delivery shaft 1224. Stated another way, at this stage in the method of use, delivery shaft 1224 is advanced in conjunction with delivery catheter 1226. Distal tip component 1234 is advanced into the left ventricle LV until heart valve prosthesis 101 in the reduced diameter state is centered at the native mitral valve. At this stage of delivery, capsule segment 1229 and cinch mechanism 1250 in tandem are still holding heart valve prosthesis 101 in a reduced diameter state.

Figure 20:
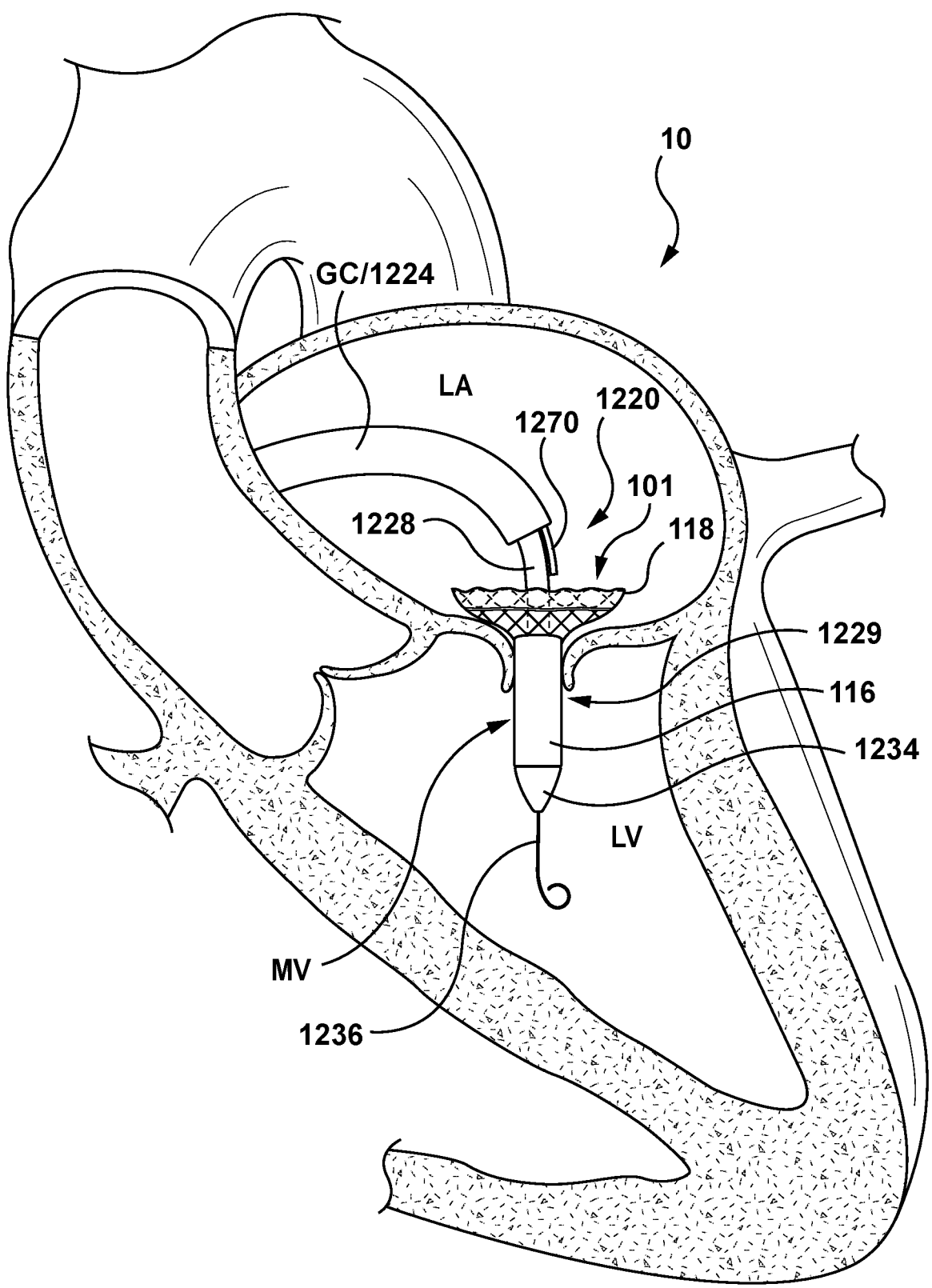
FIG. 20 is an illustration of the delivery system of FIG. 12 in situ, wherein a first stage of deployment of the heart valve prosthesis is shown in which the cinch mechanism of the delivery system has been released to deploy an inflow end of the heart valve prosthesis.

Once heart valve prosthesis 101 is positioned within the mitral valve MV, cinch mechanism 1250 is released and inflow portion 118 of heart valve prosthesis 101 (which includes at least brim 112 of heart valve prosthesis 101) is no longer retained by suture 1252 as shown in FIG. 20. Actuation of cinch mechanism 1250 provides slack or releases suture 1252 to permit inflow portion 118 of heart valve prosthesis 101 to return to an expanded state within an atrial area of the native mitral valve MV. When inflow portion 118 of heart valve prosthesis 101 deploys, at least brim 112 of heart valve prosthesis 101 radially expands. In addition to brim 112, an inflow end of valve support 110 and/or anchoring member 108 may also partially radially expand in order to permit full radial expansion of brim 112. Actuation of cinch mechanism 1250 and subsequent deployment of inflow portion 118 of heart valve prosthesis 101 may be considered a first stage of deployment of a two-stage deployment process for heart valve prosthesis 101. After release of suture 1252, capsule segment 1229 maintains outflow portion 116 of heart valve prosthesis 101 (which includes anchoring member 108 and valve support 110) in the reduced diameter state. After release of suture 1252, it may be desirable to distally advance and/or proximally retract outer shaft component 1228 independent of delivery shaft 1224 of guide catheter GC to finely adjust the position or height of the deployed brim 112 relative to the annulus of the native mitral valve.

Figure 21:
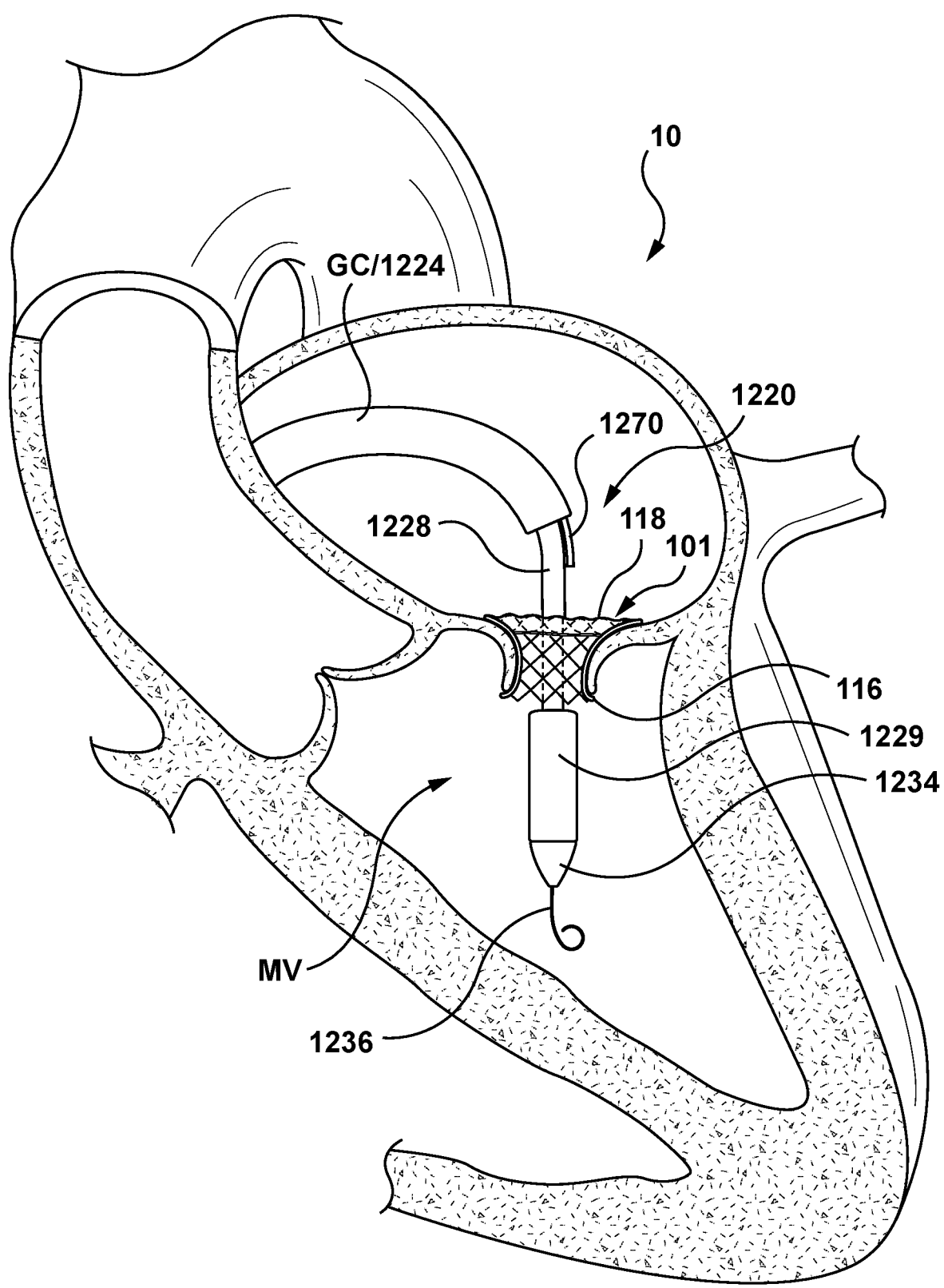
FIG. 21 is an illustration of the delivery system of FIG. 12 in situ, wherein a second stage of deployment of the heart valve prosthesis is shown in which the capsule segment of the delivery system has been distally advanced to deploy an outflow end of the heart valve prosthesis.

With reference to FIG. 21, heart valve prosthesis 101 is then fully deployed or expanded into apposition with the annulus of the native mitral valve. FIG. 21 is an illustration of a second stage of deployment of heart valve prosthesis 101 in which capsule segment 1229 has been distally advanced to deploy outflow portion 116 of heart valve prosthesis 101. More particularly, fluid is injected through lumen 1227 into cavity 1274 in order to drive capsule segment 1229 distally as described above with respect to FIG. 12 and FIG. 12B. Capsule segment 1229 is longitudinally repositioned (distally advanced in this embodiment) to expose and release outflow portion 116 of heart valve prosthesis 101, thereby permitting outflow portion 116 of heart valve prosthesis 101 to return to an expanded state within an annulus of the native mitral valve MV. When outflow portion 116 of heart valve prosthesis 101 deploys, anchoring member 108 and valve support 110 of heart valve prosthesis 101 radially expands.

Although FIGS. 18-21 illustrate a mitral valve replacement, delivery system 1220 in which capsule segment 1229 and cinch mechanism 1250 in tandem hold heart valve prosthesis 101 in a reduced diameter state may be utilized for delivering other valve prostheses for replacement of the respective native valve such as but not limited to an aortic valve prosthesis. In addition, although the two-stage deployment process is illustrated in FIGS. 18-21 with deployment of inflow portion 118 of heart valve prosthesis 101 deployed via release of cinch mechanism 1250 prior to deployment of outflow portion 116 of heart valve prosthesis 101 deployed via distal advancement of capsule segment 1229, in another embodiment hereof the capsule segment may be distally advanced prior to release of the cinch mechanism such that the outflow portion 116 of heart valve prosthesis 101 is deployed prior to the inflow portion 118 of heart valve prosthesis 101. The order or sequence of the two-stage deployment is dependent upon a patient's anatomy and application, for example depending upon which valve is being replaced (i.e., mitral, aortic, tricuspid, or pulmonary valve) and the configuration of the heart valve prosthesis.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A delivery system for delivering a heart valve prosthesis comprising:
   a heart valve prosthesis; and
   a delivery catheter having an initial delivery configuration configured for delivery within a vasculature to a treatment site, the delivery catheter including,
      a capsule segment configured to encircle a first portion of the heart valve prosthesis and to thereby hold the first portion of the heart valve prosthesis in a reduced diameter state for delivery to the treatment site, and
      a cinch mechanism including at least one suture surrounding a second portion of the heart valve prosthesis and configured to hold the second portion of the heart valve prosthesis in a reduced diameter state for delivery to the treatment site, wherein the second portion of the heart valve prosthesis is held in the reduced diameter state solely by the cinch mechanism when the delivery catheter is in the initial delivery configuration,
      wherein the capsule segment and the cinch mechanism are disposed longitudinally adjacent to each other and do not overlap when the delivery catheter is in the initial delivery configuration.

2. The delivery system of claim 1, wherein the delivery catheter further includes an outer shaft component and an inner shaft component, the outer shaft component including the capsule segment and the inner shaft component having a proximal segment positioned within the outer shaft component and a distal segment disposed distal of the capsule segment of the outer shaft component, wherein the second portion of the heart valve prosthesis is disposed along the distal segment of the inner shaft component.

3. The delivery system of claim 2, wherein the second portion of the heart valve prosthesis includes a prosthetic valve component of the heart valve prosthesis.

4. The delivery system of claim 3, wherein the capsule segment of the outer shaft component ends proximal of at least the prosthetic valve component when the delivery catheter is in the initial delivery configuration.

5. The delivery system of claim 2, wherein the capsule segment of the outer shaft component is proximally retractable relative to the inner shaft component to permit at least the first portion of the heart valve prosthesis to return to an expanded state and wherein after expansion of at least the first portion of the heart valve prosthesis the cinch mechanism maintains the second portion of the heart valve prosthesis in the reduced diameter state about the inner shaft component.

6. The delivery system of claim 1, wherein the first portion of the heart valve prosthesis is an inflow portion and the second portion of the heart valve prosthesis is an outflow portion.

7. The delivery system of claim 1, wherein the cinch mechanism is comprised of one or more sutures that are configured to compress the second portion of the heart valve prosthesis into the reduced diameter state when the delivery catheter is in the initial delivery configuration.

8. The delivery system of claim 7, wherein the one or more sutures extend to a proximal end of the delivery catheter and are releasable to permit the second portion of the heart valve prosthesis to return to an expanded state.

9. The delivery system of claim 1, wherein the first portion of the heart valve prosthesis is an outflow portion and the second portion of the heart valve prosthesis is an inflow portion.

10. The delivery system of claim 9, wherein the capsule segment is configured to be distally advanced to permit at least the first portion of the heart valve prosthesis to return to an expanded state and wherein after expansion of at least the second portion of the heart valve prosthesis the capsule segment maintains the first portion of the heart valve prosthesis in the reduced diameter state.

11. A delivery catheter for a heart valve prosthesis, the delivery catheter having an initial delivery configuration configured for delivery within a vasculature to a treatment site, the delivery catheter comprising:
   a first tubular shaft with a capsule segment; and
   a second tubular shaft having a proximal segment positioned within the first tubular shaft and a distal segment disposed distal of the capsule segment of the first tubular shaft; and
   a cinch mechanism including at least one suture disposed about the distal segment of the second tubular shaft, wherein the capsule segment and the cinch mechanism are configured in tandem to hold a heart valve prosthesis in a reduced diameter state, wherein the heart valve prosthesis is held in the reduced diameter state solely by the cinch mechanism along the distal segment of the second tubular shaft when the delivery catheter is in the initial delivery configuration.

12. The delivery catheter of claim 11, wherein the capsule segment is configured to compress a first portion of a heart valve prosthesis in a reduced diameter state and the cinch mechanism is configured to compress a second portion of a heart valve prosthesis in a reduced diameter state such that the delivery catheter permits two-stage deployment of the heart valve prosthesis.

13. The delivery system of claim 12, wherein the first portion of the heart valve prosthesis is an inflow portion and the second portion of the heart valve prosthesis is an outflow portion.

14. The delivery catheter of claim 12, wherein the cinch mechanism is comprised of one or more sutures that are configured to compress a second portion of a heart valve prosthesis into a reduced diameter state when the delivery catheter is in the initial delivery configuration and wherein the one or more sutures extend to a proximal end of the delivery catheter and are releasable to permit a second portion of a heart valve prosthesis to return to an expanded state.

15. The delivery catheter of claim 11, wherein the capsule segment ends proximal of the cinch mechanism when the delivery catheter is in the initial delivery configuration.

16. The delivery catheter of claim 11, wherein the capsule segment is proximally retractable relative to the second tubular shaft to permit a first portion of a heart valve prosthesis to return to an expanded state and wherein after expansion of at least the first portion of the heart valve prosthesis the cinch mechanism maintains a second portion of the heart valve prosthesis in the reduced diameter state about the second tubular shaft.

17. A method of deploying a heart valve prosthesis comprising:
    loading a heart valve prosthesis onto a delivery catheter, wherein the delivery catheter includes a capsule segment configured to hold a first portion of the heart valve prosthesis in a reduced diameter state and a cinch mechanism configured to hold a second portion of the heart valve prosthesis in a reduced diameter state, the cinch mechanism including at least one suture, wherein the capsule segment and the cinch mechanism are disposed longitudinally adjacent to each other and do not overlap when the delivery catheter is in an initial delivery configuration;
    advancing the delivery catheter in the initial delivery configuration through a vasculature with the first portion of the heart valve prosthesis held in the reduced diameter state by the capsule segment and the second portion of the heart valve prosthesis held in the reduced diameter state by the cinch mechanism until the heart valve prosthesis is positioned at a native heart valve, wherein the second portion of the heart valve prosthesis is held in the reduced diameter state solely by the cinch mechanism during the step of advancing the delivery catheter through the vasculature;
    longitudinally repositioning the capsule segment to permit the first portion of the heart valve prosthesis to return to an expanded state; and
    releasing the cinch mechanism to permit the second portion of the heart valve prosthesis to return to an expanded state.

18. The method of claim 17, wherein the native heart valve is a native mitral valve.

19. The method of claim 18, wherein the first portion of the heart valve prosthesis is an inflow portion and the second portion of the heart valve prosthesis is an outflow portion, and wherein the step of longitudinally repositioning the capsule segment permits the inflow portion of the heart valve prosthesis to return to an expanded state within an atrial area of the native mitral valve and the step of releasing the cinch mechanism permits the outflow portion of the heart valve prosthesis to return to an expanded state within an annulus of the native mitral valve.

20. The method of claim 18, wherein the step of advancing the delivery catheter through the vasculature includes a transseptal delivery approach to the native mitral valve.

* * * * *